(12) United States Patent
Hardick et al.

(10) Patent No.: US 10,850,259 B2
(45) Date of Patent: Dec. 1, 2020

(54) CHROMATOGRAPHY MEDIUM

(71) Applicant: Puridify Ltd., Hertfordshire (GB)

(72) Inventors: Oliver Hardick, London (GB); Daniel Gilbert Bracewell, London (GB); Stewart Dods, London (GB)

(73) Assignee: Puridify Ltd., Stevenage (GB)

( * ) Notice: Subject to any disclaimer, the term of this patent is extended or adjusted under 35 U.S.C. 154(b) by 133 days.

(21) Appl. No.: 15/091,158

(22) Filed: Apr. 5, 2016

(65) Prior Publication Data

US 2016/0288089 A1 Oct. 6, 2016

Related U.S. Application Data

(63) Continuation-in-part of application No. PCT/GB2014/000401, filed on Oct. 9, 2014, and a
(Continued)

(51) Int. Cl.
*B01J 20/26* (2006.01)
*B01D 15/32* (2006.01)
(Continued)

(52) U.S. Cl.
CPC .......... *B01J 20/265* (2013.01); *B01D 15/327* (2013.01); *B01D 15/361* (2013.01); *B01D 15/362* (2013.01); *B01D 15/363* (2013.01); *B01D 15/38* (2013.01); *B01D 15/3804* (2013.01); *B01D 15/3809* (2013.01); *B01D 15/3819* (2013.01);
(Continued)

(58) Field of Classification Search
CPC .......... G01N 30/482; G01N 2030/484; G01N 30/6069; G01N 30/6091; G01N 30/02; G01N 30/48; G01N 30/6052
See application file for complete search history.

(56) References Cited

U.S. PATENT DOCUMENTS

| 5,514,818 A | 5/1996 | Tachibana |
| 5,863,428 A | 1/1999 | Ma et al. |

(Continued)

FOREIGN PATENT DOCUMENTS

| DE | 19629208 | 1/1998 |
| EP | 0372581 A2 | 6/1990 |

(Continued)

OTHER PUBLICATIONS

Hardick (Biotechnology and Bioengineering, vol. 110, No. 4, Apr. 2013, pp. 1119-1128, Published Online Nov. 1, 2012) http://onlinelibrary.wiley.com/doi/10.1002/bit.24765/epdf.*
(Continued)

*Primary Examiner* — Neil N Turk
(74) *Attorney, Agent, or Firm* — Eversheds Sutherland (US) LLP

(57) ABSTRACT

The present invention provides a process for preparing a functionalised polymeric chromatography medium, which process comprises (I) providing two or more non-woven sheets stacked one on top of the other, each said sheet comprising one or more polymer nanofibres, (II) simultaneously heating and pressing the stack of sheets to fuse points of contact between the nanofibres of adjacent sheets, and (III) contacting the pressed and heated product with a reagent which functionalises the product of step (II) as a chromatography medium.

14 Claims, 21 Drawing Sheets

Related U.S. Application Data continuation-in-part of application No. PCT/GB2013/052626, filed on Oct. 9, 2013, said application No. PCT/GB2014/000401 is a continuation-in-part of application No. PCT/GB2013/052626, filed on Oct. 9, 2013.

(51) Int. Cl.

| | | |
|---|---|---|
| *B01J 20/24* | (2006.01) | |
| *B01D 39/16* | (2006.01) | |
| *B01D 15/38* | (2006.01) | |
| *B29C 65/02* | (2006.01) | |
| *B32B 37/06* | (2006.01) | |
| *C07K 1/18* | (2006.01) | |
| *B01J 20/285* | (2006.01) | |
| *B01J 20/30* | (2006.01) | |
| *B01D 15/36* | (2006.01) | |
| *B01J 20/28* | (2006.01) | |
| *B01J 39/05* | (2017.01) | |
| *B01J 41/13* | (2017.01) | |
| *B01J 41/07* | (2017.01) | |
| *B01J 39/19* | (2017.01) | |
| *B01D 39/14* | (2006.01) | |
| *B01J 20/287* | (2006.01) | |
| *B01J 20/288* | (2006.01) | |
| *B01J 39/26* | (2006.01) | |
| *B01J 41/20* | (2006.01) | |
| *B29C 65/00* | (2006.01) | |
| *B32B 5/02* | (2006.01) | |
| *B32B 27/08* | (2006.01) | |
| *B32B 27/12* | (2006.01) | |
| *B32B 27/32* | (2006.01) | |
| *B32B 37/10* | (2006.01) | |
| *B32B 37/18* | (2006.01) | |
| *C07K 1/16* | (2006.01) | |
| *C07K 1/20* | (2006.01) | |
| *C07K 1/22* | (2006.01) | |
| *C12M 1/12* | (2006.01) | |
| *B29K 601/00* | (2006.01) | |
| *B29K 627/18* | (2006.01) | |
| *B29L 9/00* | (2006.01) | |

(52) U.S. Cl.
CPC ............. *B01D 39/14* (2013.01); *B01D 39/16* (2013.01); *B01D 39/1623* (2013.01); *B01J 20/24* (2013.01); *B01J 20/285* (2013.01); *B01J 20/287* (2013.01); *B01J 20/28007* (2013.01); *B01J 20/288* (2013.01); *B01J 20/28033* (2013.01); *B01J 20/28038* (2013.01); *B01J 20/28083* (2013.01); *B01J 20/28085* (2013.01); *B01J 20/3007* (2013.01); *B01J 20/3085* (2013.01); *B01J 39/05* (2017.01); *B01J 39/19* (2017.01); *B01J 39/26* (2013.01); *B01J 41/07* (2017.01); *B01J 41/13* (2017.01); *B01J 41/20* (2013.01); *B29C 65/02* (2013.01); *B29C 66/45* (2013.01); *B29C 66/712* (2013.01); *B29C 66/7294* (2013.01); *B32B 5/022* (2013.01); *B32B 27/08* (2013.01); *B32B 27/12* (2013.01); *B32B 27/322* (2013.01); *B32B 37/06* (2013.01); *B32B 37/10* (2013.01); *B32B 37/182* (2013.01); *C07K 1/165* (2013.01); *C07K 1/18* (2013.01); *C07K 1/20* (2013.01); *C07K 1/22* (2013.01); *B01J 2220/54* (2013.01); *B29K 2601/12* (2013.01); *B29K 2627/18* (2013.01); *B29K 2713/00* (2013.01); *B29L 2009/00* (2013.01); *B32B 2262/04* (2013.01); *B32B 2317/18* (2013.01); *B32B 2327/18* (2013.01); *C07K 1/16* (2013.01); *C12M 25/14* (2013.01)

(56) References Cited

U.S. PATENT DOCUMENTS

| | | | |
|---|---|---|---|
| 6,790,528 B2 | 9/2004 | Wendorff et al. | |
| 6,841,097 B2 | 1/2005 | Andersson et al. | |
| 6,923,908 B1 * | 8/2005 | Thompson | B01D 39/083 |
| | | | 210/188 |
| 7,655,070 B1 * | 2/2010 | Dallas | B01D 39/04 |
| | | | 95/154 |
| 7,723,084 B2 | 5/2010 | Wang et al. | |
| 9,215,891 B2 | 12/2015 | Nazir et al. | |
| 2006/0065583 A1 | 3/2006 | Buckley et al. | |
| 2006/0093820 A1 | 5/2006 | Margarit-Puri et al. | |
| 2011/0017611 A1 | 1/2011 | Menozzi et al. | |

FOREIGN PATENT DOCUMENTS

| | | |
|---|---|---|
| EP | 1614795 | 1/2006 |
| JP | S60-136522 A | 7/1985 |
| JP | H01-120903 U | 8/1989 |
| JP | H03-503212 A | 7/1991 |
| JP | 2005-315668 A | 11/2005 |
| JP | 2008-127409 A | 6/2008 |
| JP | 2011-058859 A | 3/2011 |
| JP | 2013-068594 A | 4/2013 |
| WO | WO 2003/106655 | 12/2003 |
| WO | WO 2010/030900 | 3/2010 |
| WO | WO 2013/068741 | 5/2013 |

OTHER PUBLICATIONS

Ma et al. Electrospun cellulose nanofiber as affinity membrane, Journal of Membrane Science, Jun. 23, 2005, pp. 115-123 (Year: 2005).*

Ma et al. Electrospun polyethersuflone affinity membrane: Membrane preparation and performance evaluation, Journal of Chromatography B, Sep. 17, 2009, pp. 3686-3694 (Year: 2009).*

Zhang et al. Fabrication and bioseparation studies of adsorptive membranes/felts made from electrospun cellulose acetate nanofibers, Journal of Membrane Science, Mar. 27, 2008, pp. 176-184 (Year: 2008).*

Bilad et al. Assessment and optimization of electrospun nanofiber-membranes in a membrane bioreactor (MBR), Journal of Membrane Science, Jul. 7, 2011, pp. 181-191 (Year: 2011).*

"HiTrap Blue HP" GE Healthcare Life Sciences, accessed from the internet on Oct. 31, 2017.

Aumann et al., "A Continuous Multicolumn Countercurrent Solvent Gradient Purification (MCSGP) Process," *Biotechnology and Bioengineering*, 98(5):1043-1055, (2007).

Bilad et al., "Assessment and Optimization of Electrospun Nanofiber-Membranes in a Membrane Bioreactor (MBR)," *Journal of Membrane Science*, 380:181-191, (2011).

Charcosset et al., "Membrane Chromatography," *Membrane Processes in Biotechnology and Pharmaceutics*, 169-212, (2012).

Charcosset et al., "Purification of proteins by membrane chromatography," *J. Chem. Technol. Biotechnol.*, 71:95-110, (1998).

Charcosset, "Membrane Processes in Biotechnology: An Overview," *Biotechnology Advances*, 24:482-492, (2006).

Charcosset, "Membrane Systems and Technology," *Comprehensive Biotechnology, 2nd Edition*, Ed. Murray Moo-Young, pp. 603-618, (2011).

Clark et al., "Technique for Ultrathin Layer chromatography Using and Eltrospun, Nanofibrous stationary Phase," *Analytical Chemistry*, 81:4121-4129, (2009).

Communication under Rule 71(3) issued in European Patent Application No. 14786703.0, dated Sep. 14, 2016.

Coskun, "Separation techniques: Chromatography," *North Clin Istanbul*, 3(2):156-160, (2016).

(56) References Cited

OTHER PUBLICATIONS

Cossins et al., "Recombinant production of a $V_L$ single domain antibody in *Escherichia coli* and analysis of its interaction with peptostreptococcal protein L," *Protein Expression and Purification*, 51:253-259, (2007).
Dods et al., "Characterization of Electrospun Cellulose Acetate Nanofiber Adsorbers for Bioseparation" presented at 245$^{th}$ ACS National Meeting & Exposition, Apr. 9, 2013.
Dods et al., "Derivitization of electrospun cellulose nanofiber adsorbers for bioseparation," 245$^{th}$ American Chemical Society National Meetings & Exposition, Chemistry of Energy and Food, Apr. 9, 2013.
European Search Report issued in European Patent application No. 17154671.6, dated Jun. 2, 2017.
Farid "Establishing Bioprocesses for Producing Antibodies as a Basis for Future Planning," *Adv. Biochemical Engineering, Biotechnology*, 101:1-42, (2006).
Ghosh, "Protein separation using membrane chromatography: opportunities and challenges," *J. Chromatogr. A*., 952:13-27, (2002).
Gottschalk et al., "Bioseparation in Antibody Manufacturing: The Good, the Bad and the Ugly," *Biotechnology Progress*, 24:496-503, (2008).
Guest et al., "Evaluation of simulated moving bed chromatography for pharmaceutical process development," *J. Chromatogr. A*, 760:159-162, (1997).
Hahn et al., "Mass transfer properties of monliths," *Sep. Sci. Technol.*, 37(7):1545-1565, (2002).
Hardick et al., "Nanofibre adsorbents for High Productivity Downstream Processing," *Biotechnology and Bioengineering*, 110(4):1119-1128, (2013).
Hardick et al., "Nanofibre fabrication in a temperature and humidity controlled environment for improved fibre consistency," *Journal of Materials Science*, 46(11):3890-3898, (2011).
International Preliminary Report on Patentability issued in International Patent Application No. PCT/GB2013/052626, dated Apr. 12, 2016.
International Preliminary Report on Patentability issued in International Patent Application No. PCT/GB2014/000401, dated Apr. 12, 2016.
International Preliminary Report on Patentability issued in International Paten Application No. PCT/GB2012/052768, dated May 12, 2014.
International Search Report and Written Opinion issued in International Patent Application No. PCT/GB2013/052626, dated Aug. 21, 2014.
International Search Report and Written Opinion issued in International Patent Application No. PCT/GB2014/000401, dated Dec. 22, 2014.
International Search Report and Written Opinion issued in International Patent Application No. PCT/GB2012/052768, dated Feb. 2, 2013.
Invitation to Pay Additional Fees issued in International Patent Application No. PCT/GB2013/052626, dated May 8, 2014.
Jungbauer et al., "Chromatographic Media for Bioseparation", *J. Chromatogr. A*, 1065:3-12, (2005).
Kalbfuss et al., "Direct capture of influenza A virus from cell culture supernatant with Sartobind anion-exchange membrane adsorbers", *J. Membr. Sci.*, 299:251-260, (2007).
Kaur et al., "Plasma-induced graft copolymerization of poly(methacrylic acid) on electrospun poly(vinylidene fluoride) nanofiber membrane," *Langmuir*, 23(26):13085-13092, (2007).
Lascu et al., "Ion-exchange properties of cibacron blue 3G-A sepharose (blue sepharose) and the interaction of proteins with cibacron blue 3g-a", *Journal of Chromatography A*, 283:199-210, (1984).
Levison, "Large scale ion-exchange column chromatography of proteins: comparison of different formats", *J. Chromatogr. B.*, 790:17-33, (2003).
Ma et al., "Electrospun cellulose nanofiber as affinity membrane," *Journal of Membrane Science*, 265:115-123, (2005).
Ma et al., "Electrospun polyethersulfone affinity membrane: Membrane preparation and performance evaluation," *J. Chromatograph. B.*, 877:3686-3694, (2009).
Ma et al., "Electrospun regenerated cellulose nanofiber affinity membrane functionalized with protein A/G for IgG purification," *Journal of Membrane Science*, 319:23-28, (2008).
Matsumoto et al., "Preparation of ion-exchange fiber fabrics by electrospray deposition," *Journal of Colloid and Interface Sciences*, 293:143-150, (2006).
Menkhaus et al., "Electrospun nanofiber membranes surface functionalized with 3-dimensional nanolayers as an innovative adsorption medium with ultra-high capacity and throughput," *Chem. Chommu.*, 46:3720-3722, (2010).
Nakagaito et al., "Production of microfibrillated cellulose (MFC)-reinforced polylactic acid (PLA) nanocomposites from sheets obtained by a papermaking-like process," *Composites Science and Technology*, 69:1293-1297, (2009).
Nicoud et al., "Simulated moving bed chromatography for preparative separations," *LC-GC* 18(7):680-687, (2000).
Niven et al., "A method for the continuous purification of proteins by affinity adsorption," *J. Biotechnol.*, 31:179-190, (1993).
Notice of Allowance issued in U.S. Appl. No. 14/356,817, dated Jun. 27, 2017.
Office Action issued in European Patent Application No. 12784664.0, dated May 11, 2017.
Office Action issued in European Patent Application No. 12784664.0, dated Apr. 4, 2018.
Office Action issued in U.S. Appl. No. 14/356,817, dated Aug. 1, 2016.
Office Action issued in U.S. Appl. No. 14/356,817, dated Dec. 2, 2016.
Phillips et al., "Performance of a membrane adsorber for trace impurity removal in biotechnology manufacturing,". *Chromatogr. A.*, 1078:74-82, (2005).
Rathore et al., "Recent Developments in Membrane-Based Separations in Biotechnology Processes: Review," *Preparative Biochemistry & Biotechnology*, 41:398-421, (2011).
Record of Telephone Consultation issued in European Patent Application No. 14786703.0, dated Sep. 6, 2016.
Roque et al., "An article protein L for the purification of immunoglobulins and Fab fragments by affinity chromatography," *Journal of Chromatography A*, 1064:157-167, (2005).
Ruthven et al., "Review article No. 31, Counter-Current and Simulated Counter Current Adsorption Process," *Chem. Eng. Sci.*, 44(5):1011-1038, (1989).
Sarfert et al., "Mass transfer limitations in protein separations using ion-exchange membranes," *J. Chromatogr. A*., 764:3-20, (1997).
Schulte et al., "Preparative enantioseparation by simulated moving bed chromatography," *J. Chromatogr. A*, 906:399-416, (2001).
Search Report issued in Great Britain Patent Application No. GB1119192.1, dated Mar. 1, 2012.
Shi et al., "Mathematical analysis of affinity membrane chromatography," *J. Crhomatogr. A.*, 1081:156-162, (2005).
Ströhlein et al., "Continuous Processing: The Multicolumn Countercurrent Solvent Gradient Purification Process: A continuous chromatographic process for monoclonal antibodies without using Protein A," biopharma international, Feb. 2, 2007, 5 pages, Available at: <http://biopharminternational.findpharma.com/biopharma.com/biopharm/article/articleDetail.jsp?is=401628&sk=&date=&pageID=3 >.
Subramanian (Ed.), "Continuous Chromatography in Downstream Processing of Products of Biotechnology and Natural Origin," *Bioseparation and Bioprocessing*, vol. 1: Germany: Wiley-VCH, pp. 225-255, (2007).
Subramanian et al., "Dye-Ligand Affinity Chromatography: The Interaction of Cibacron Blue F3GA® with Proteins and Enzyme," *Critical Reviews in Biochemistry*, 16(2):169-205, (1984).
Tejeda et al., "Optimal design of affinity membrane chromatographic columns", *J. chromatogr. A.*, 830: 293-300, (1999).
Tennikov et al., "Effect of porous structure of macroporous polymer supports on resolution in high-performance membrane chromatography of proteins," *J. Chromatogr. A.*, 798:55-64, (1998).

(56) References Cited

OTHER PUBLICATIONS

Turner, "A Simple and Colourful Procedure to Demonstrate the Principles of affinity Chromatography," *Biomedical Education*, 7(3):60-62, (1979).

Weissenborn et al., "A study of combined filtration and adsorption of nylon-based dye-affinity membranes: separation of recombinant L-alanine dehydrogenase form crude fermentation broth," *Biotehcnol. Appl. Biochem.*, 25:159-168, (1997).

Wilcheck et al., "Thirty years of affinity chromatography," *Reactive and Functional Polymers*, 41:263-268, (1999).

Written Opinion issued in Singaporean Patent Application No. 11201602195Y, dated Dec. 21, 2016.

Zhang et al., "Fabrication and bioseparation Studies of adsorptive Membranes/Felts Made From Electrospun Cellulose Acetate Nanofibres", *Journal of Membrane Sciences*, 319:176-184, (2008).

Zheng et al., "Control of Pore Sizes in Macroporous Chitosan and Chitin Membranes," *Ind. Eng. Chem. Res.*, 35:4169-4175, (1996).

Zhou et al., "Basic Concepts in Q Membrane Chromatography for Large-Scale Antibody Production," *Biotechnol. Prog.*, 22:341-349, (2006).

Ziabari et al., "Evaluation of electrospun nanofiber pore structure parameters," *Korean J. Chem. Eng.*, 25(4):923-932, (2008).

Zotero Report, Search Engine Results accessed from the internet on Oct. 10, 2013.

Japanese Office Action for JP Application No. 2016-547243 dated Jul. 24, 2018 (4 pages).

* cited by examiner

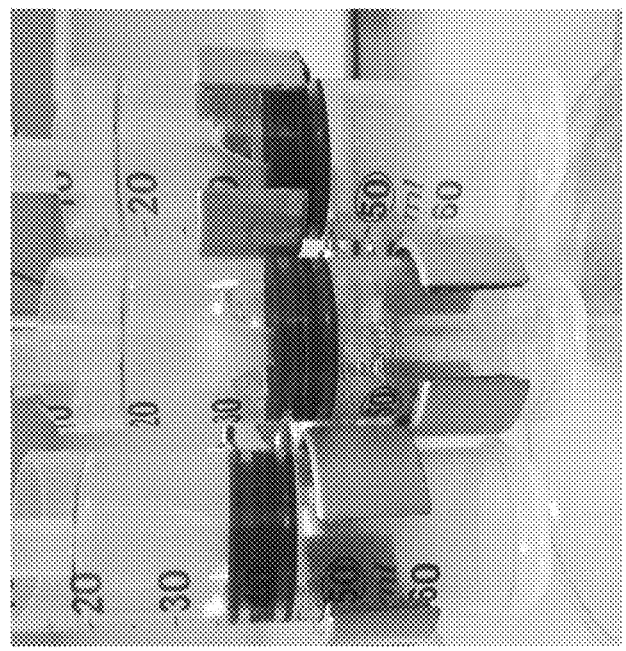
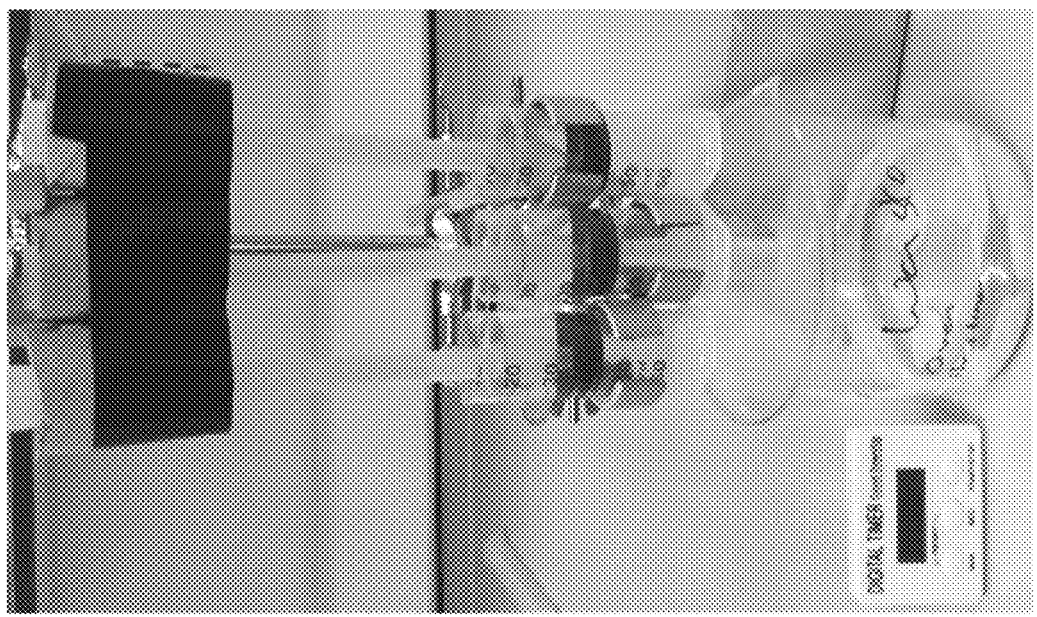
FIGURE 3

FIGURE 4
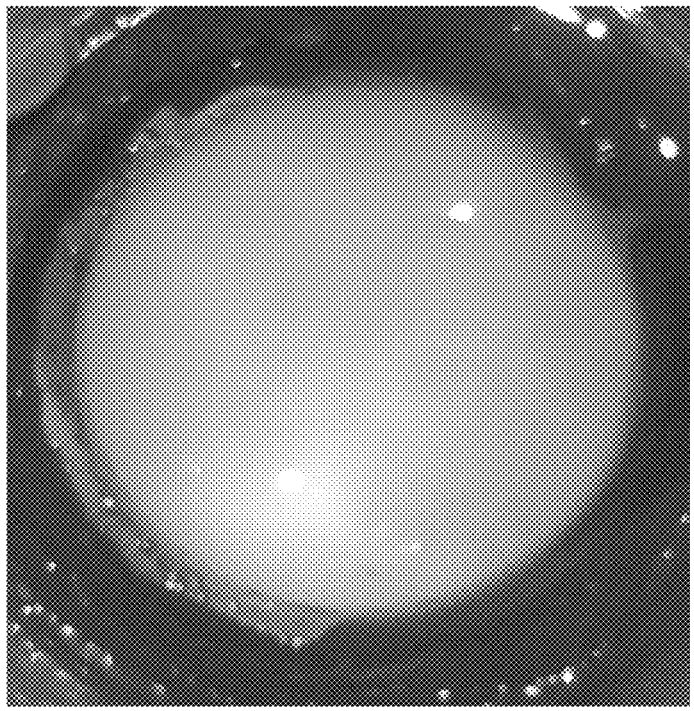
After 120 hours, "press"
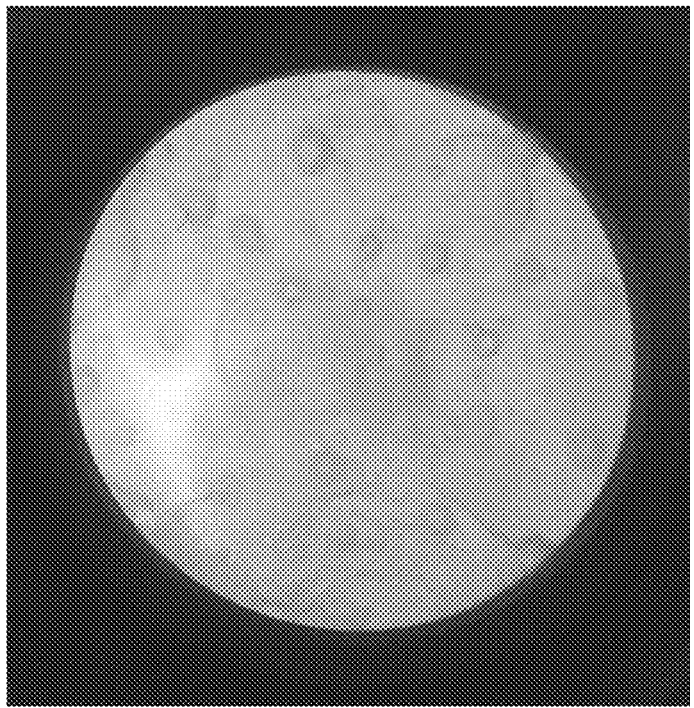
After 10 minutes, "Oven"

CHROMATOGRAPHY MEDIUM

CROSS REFERENCE TO RELATED APPLICATIONS

The present application is a continuation-in-part of International Application No. PCT/GB2014/000401 filed Oct. 9, 2014, and the present application is a continuation-in-part of International Application No. PCT/GB2013/052626 filed Oct. 9, 2013, and International Application No. PCT/GB2014/000401 filed Oct. 9, 2014 is a continuation-in-part of International Application No. PCT/GB2013/052626 filed Oct. 9, 2013, all of which applications are incorporated herein by reference in their entirety.

FIELD OF THE INVENTION

The invention relates to functionalised chromatography media which are suitable for isolating biological molecules from mobile phases.

BACKGROUND TO THE INVENTION

The biotechnology market is the fastest growing sector within the world pharmaceutical market, accounting for 20% ($153 bn) of all market sales in 2012. This growth from 10% of the market share in 2002 is set to grow by 41% between 2012 and 2018 from $153 bn to $215 bn. There are currently around 200 monoclonal antibody (MAb) products on the market and with over 1000 in clinical trials the need for technological advancement in this area is clear. Over the last decade typical fermentation titres of biomolecules have grown from 0.5 g/L-50 g/L, and while the downstream purification processes have also received some research and development, improvements in this area have not matched those in the upstream. The heavily relied on bind/elute chromatography unit operations are, in economic terms, the key to advancements in the downstream processing of biomolecules, such as MAbs. Chromatography accounts for a very significant part of the downstream processing costs of biomolecules, which in turn impacts on the overall costs of the biomolecules themselves.

Historically, conventional packed bed chromatography has been an extremely powerful separation tool. However, it is becoming ever more apparent that radically new systems must be employed to allow biomolecules to be recovered efficiently and economically after preparation.

One area which has seen development is the synthesis of new ligands to replace current expensive affinity ligands.

Another route which has been explored is modification of conventional support structures such as porous beaded packed bed adsorbents. This is typically to address drawbacks associated with such adsorbents, in particular problems with pressure drop and residence times. These drawbacks typically result in inefficient separations. The development of new adsorbent structures that allow for flowrate independent operation offers the advantage of increased throughput, but has generally only proven useful at small scale. Issues with adsorbent fouling are common, and this often limits chromatographic separation techniques to late stage polishing operations. A trade-off must be made between fouling and capture capacity with regard to adsorbent pore sizes. Small pore sizes are required for good separation with sharp breakthrough curves but result in increased fouling. Conversely, larger pore size adsorbents (10 µm-150+µm) may offer better handling of foulants but small target biomolecules may pass through such an adsorbent without binding.

More recently, membrane chromatography has been reported as a potentially viable alternative in contaminant capture mode.

Another focus of research has been the development of monolith structures which have proved to offer good separation for large biomolecules such as plasmids and viruses due to the relatively large pores present on the surface. The current industry trend to move towards single-use systems favours membrane chromatography as the economics of single-use membranes are more favourable than single-use packed bed columns.

Another route for development is a move into continuous processing. The drive towards continuous processing may allow efficiencies to be achieved in many systems. Thus, continuous operation presents opportunities for real-time process monitoring and automated control with potential benefits including predictable product specification, reduced labour costs, and integration with other continuous processes. However, little in the way of truly continuous chromatography operation has been developed thus far.

It will therefore be appreciated that there are many different avenues of research being employed to provide improved processes for recovering biomolecules.

Electrospun polymeric nanofibres have properties which offer one potential solution to the issues observed with conventional support matrices used in downstream bioprocessing. Their properties readily lend themselves to ligand support surfaces with the potential for high capacity and high mass transfer rate operations, thus yielding flowrate independent binding with a high porosity and relatively small surface pore size system.

Adsorbent cartridges containing electrospun polymeric nanofibres with diethylaminoethyl (DEAE) functionality have been reported with binding capacities around 10% of a typical packed bed system but with flowrates around fifty times that of a typical packed bed system. Such nanofibre systems present a surface area to volume ratio similar to that of a porous beaded system. However, such existing nanofibre systems have somewhat lower binding capacities than typical packed bed systems. Known nanofibre systems also show poor reproducibility when the same membrane is used multiple times. This represents a limit on their utility in recovering biomolecules.

Thus, it has not previously been possible to prepare nanofibre adsorbent systems with binding capacities greater than around 10% of a typical packed bed system whilst retaining the porosity and robust reproducible operations associated with such nanofibre systems.

The thickness of nanofibre adsorbent systems produced by electrospinning is limited during fabrication as the deposition of nanofibres onto an earthed collector surface yields a less earthed surface as deposition increases. The residual charge in the deposited fibres therefore makes that area less attractive to continued deposition resulting in the fibres spreading further over the collector surface. This has the effect of limiting the thickness of nanofibre mats produced by electrospinning to about 100-200 µm. The limited thickness of these nanofibre mats brings with it an inherent limit in physical strength of the overall mat which limits the materials' usefulness for process applications such as chromatography.

One known nanofibre adsorbent system is described in Ma, et al, Journal of Membrane Science 265 (2005) 115-123. This document describes a process for producing a cellulose nanofibre membrane, which involves heat treating a single layer of nonwoven fibre mesh consisting of cellulose acetate nanofibres, treating the heated cellulose acetate fibres with NaOH and functionalising the resultant cellulose fibres with Cibacron Blue. Multiple membranes may be stacked together, the edges glued and the stack placed in a filter holder.

SUMMARY OF THE INVENTION

In its broadest sense, the present invention provides processes for preparing functionalised chromatography media, which process involves treating one or more polymer nanofibres with a combination of physical and chemical processing steps to yield a functionalised product that is suitable for use as a chromatography medium in a chromatography method.

It has now been found that a specific series of physical and chemical processing steps greatly increases the binding capacity of nanofibre adsorbent systems, typically increasing said binding capacity by over 250% under typical operation conditions. It has also been found that certain specific physical processing steps improve the chemical resistivity of nanofibre adsorbent systems. This means both that the adsorbent systems of the invention can be used under harsher conditions, and also that the adsorbent systems can be used multiple times without loss of performance.

Accordingly, the present invention provides a process for preparing a functionalised polymeric chromatography medium, which process comprises
(I) providing two or more non-woven sheets stacked one on top of the other, each said sheet comprising one or more polymer nanofibres,
(II) simultaneously heating and pressing the stack of sheets to fuse points of contact between the nanofibres of adjacent sheets, and
(III) contacting the pressed and heated product with a reagent which functionalises the product of step (II) as a chromatography medium.

More specifically, fusing points of contact between the nanofibres of adjacent sheets involves fusing points of contact between sections of a polymer nanofibre in a sheet with sections of a polymer nanofibre in an adjacent sheet. Typically, this also involves fusing points of contact between sections of a polymer nanofibre in a sheet with other sections of the same nanofibre.

The present invention also provides:
A functionalised chromatography medium obtainable by the process of the present invention.
A process for preparing a chromatography cartridge, which process comprises carrying out the process of the present invention and incorporating the thus-obtained product into a cartridge.
A chromatography cartridge which (a) is obtainable by said process, or (b) which comprises one or more functionalised chromatography media of the invention.
Use of a functionalised chromatography medium of the invention or a chromatography cartridge of the invention in chromatography.
A process for isolating one or more biological molecules from a mobile phase, which process comprises contacting one or more biological molecules in a mobile phase with a functionalised chromatography medium of the invention or a chromatography cartridge of the invention.

The present invention also provides a process for preparing a polymeric medium, which process comprises providing two or more non-woven sheets, as defined herein, stacked one on top of the other, each said sheet comprising one or more polymer nanofibres, as defined herein, and simultaneously heating and pressing the stack of sheets to fuse points of contact between the nanofibres of adjacent sheets as defined in herein. Also provided is a polymeric medium obtainable by that process.

BRIEF DESCRIPTION OF THE FIGURES

FIG. 3 shows an experimental set up for determining chemical stability of chromatography membranes.

FIG. 4 shows photographs of a membrane not in accordance with the invention and a membrane in accordance with the invention following exposure to NaOH.

DETAILED DESCRIPTION OF THE INVENTION

Polymer Nanofibres

Figure 1:
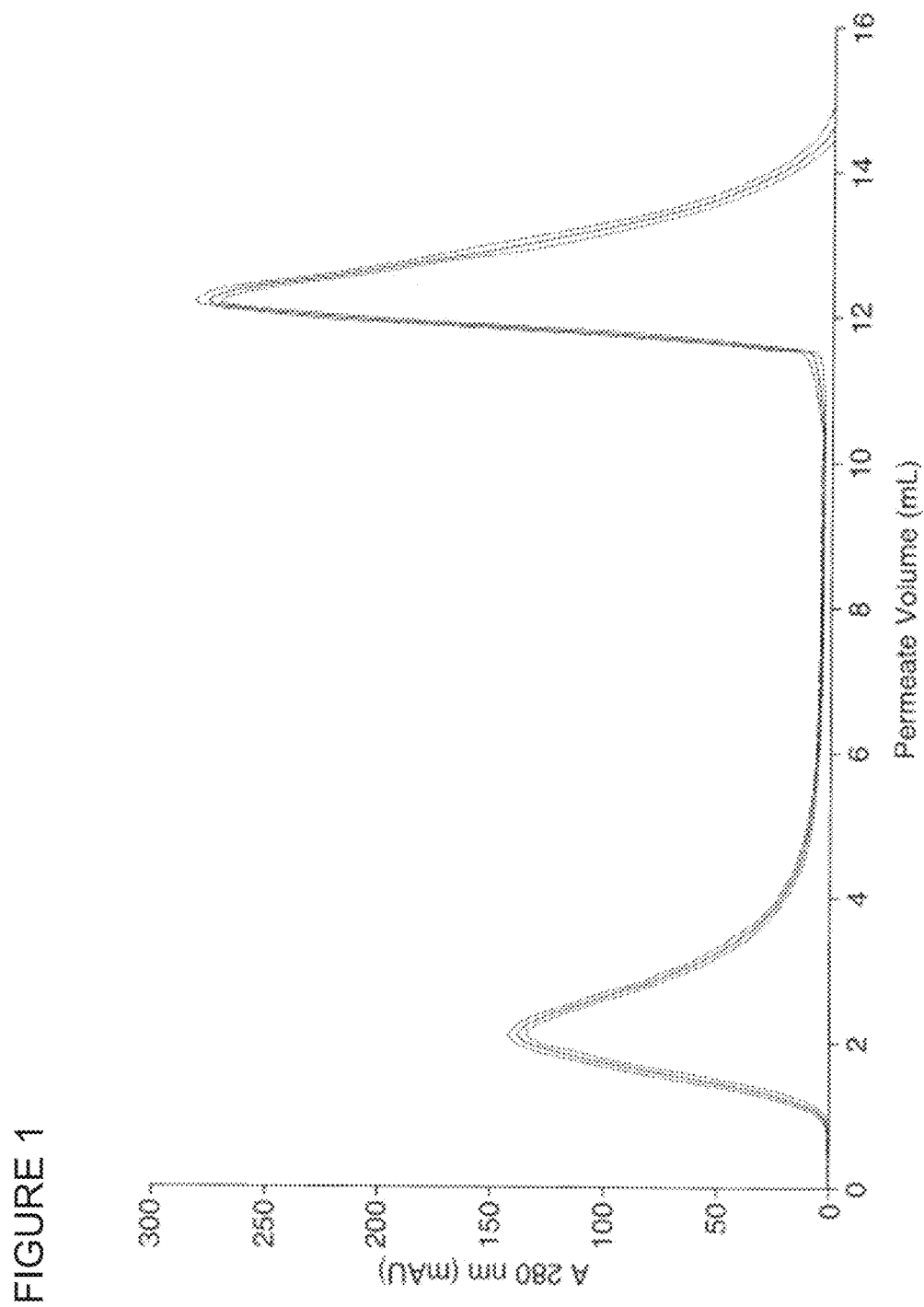
FIG. 1 shows the performance of a functionalised chromatography medium of the invention in anion exchange chromatography.

The functionalised chromatography media of the present invention are formed from one or more polymer nanofibres. The polymer nanofibres are typically electrospun polymer nanofibres. Such electrospun polymer nanofibres are well known to the person skilled in the art and optimised conditions for their production can be found in, for example, O. Hardick, et al, J. Mater. Sci. 46 (2011) 3890, the entirety of which is incorporated herein by reference. The processes of the present invention typically comprise an initial step of electrospinning a polymer to produce one or more polymer nanofibres. This may involve electrospinning a polymer to produce one or more non-woven sheets, each comprising one or more polymer nanofibres Polymer nanofibres for use in the present invention typically have mean diameters from 10 nm to 1000 nm. For some applications, polymer nanofibres having mean diameters from 200 nm to 800 nm are appropriate. Polymer nanofibres having mean diameters from 200 nm to 400 nm may be appropriate for certain applications.

The length of polymer nanofibres for use in the present invention is not particularly limited. Thus, conventional electrospinning processes can produce polymer nanofibres many hundreds of metres or even kilometres in length. Typically, though, the one or more polymer nanofibres have a length up to 10 km, preferably from 10 m to 10 km.

Typically, the one or more polymer nanofibres are provided in the form of one or more non-woven sheets, each comprising one or more polymer nanofibres. A non-woven sheet comprising one or more polymer nanofibres is a mat of said one or more polymer nanofibres with each nanofibre oriented essentially randomly, i.e. it has not been fabricated so that the nanofibre or nanofibres adopts a particular pattern. Non-woven sheets comprising polymer nanofibres are typically provided by known methods, such as that disclosed in O. Hardick, et al, J. Mater. Sci. 46 (2011) 3890. Non-woven sheets may, in certain circumstances, consist of a single polymer nanofibre. Alternatively, non-woven sheets may comprise two or more polymer nanofibres, for example 2, 3, 4, 5, 6, 7, 8, 9 or 10 polymer nanofibres.

Non-woven sheets typically have area densities from 1 to 40 $g/m_2$, preferably from 5 to 25 $g/m_2$, in some circumstances from 1 to 20 or 5 to 15 $g/m_2$.

Non-woven sheets typically have a thickness from 5 to 120 μm, preferably from 10 to 100 μm, in some circumstances from 50 to 90 μm, in other circumstances from 5 to 40, 10 to 30 or 15 to 25 μm.

The polymer used to produce the nanofibres used in the processes of the present invention is not particularly limited, provided the polymer is suitable for use in chromatography applications. Thus, typically, the polymer is a polymer suitable for use as a chromatography medium, i.e. an adsorbent, in a chromatography method. Suitable polymers include polamides such as nylon, polyacrylic acid, polymethacrylic acid, polyacrylonitrile, polystyrene, polysulfones, polycaprolactone, collagen, chitosan, polyethylene oxide, agarose, agarose acetate, cellulose, cellulose acetate, and combinations thereof. Cellulose and cellulose acetate are preferred.

Typically, the process of the present invention is for preparing a functionalised cellulose chromatography medium, and the process comprises providing one or more cellulose acetate nanofibres. Preferably, the process comprises providing one or more non-woven sheets, each comprising one or more cellulose acetate nanofibres. Cellulose acetate is readily electrospun and can readily be transformed into cellulose after electrospinning. Thus, preferably the process comprises providing one or more non-woven sheets, each comprising one or more electrospun cellulose acetate nanofibres.

Physical Modification of Nanofibres

The processes of the present invention involve physical modification of the polymer nanofibres in the non-woven sheets, namely heating and pressing, prior to chemical modification. These steps improve the structural stability of the material. The pressing and heating conditions may also be varied to alter the thickness and/or porosity of the resultant material.

Use of multiple non-woven sheets of polymer nanofibres enables a thicker material to be prepared which has a greater capacity for adsorbence (once functionalised). It has also been found that membranes produced by heating and pressing multiple non-woven sheets of polymer nanofibres have improved properties compared with stacks formed from single sheets of heat treated polymer nanofibres. Thus, the process of the present invention comprises providing two or more non-woven sheets stacked one on top of the other, each said sheet comprising one or more polymer nanofibres, and simultaneously heating and pressing the stack of sheets to fuse points of contact between the nanofibres of adjacent sheets. Thus, the process of the present invention involves providing a stack of two or more non-woven sheets, as defined herein, in step (I) and the present invention provides a process for preparing a functionalised polymeric chromatography medium, which process comprises (I) providing a stack of two or more non-woven sheets, each said sheet comprising one or more polymer nanofibres, (II) simultaneously heating and pressing the stack of sheets to fuse points of contact between the nanofibres of adjacent sheets, and (III) contacting the pressed and heated product with a reagent which functionalises the product of step (II) as a chromatography medium.

Typically, a stack of from two to thirty non-woven sheets are provided. In certain circumstances, a stack of between five and twenty five non-woven sheets may be provided. In certain circumstances, a stack of between 10 and 20 non-woven sheets may be provided. The number of non-woven sheets employed will affect the thickness of the eventual chromatography medium, and its permeability to liquids. Thus, a thicker medium will generally have a lower permeability than a thinner medium. Thus, where a high permeability is required, typically a lower number of sheets are employed. Where a lower permeability medium is required a higher number of sheets may be employed.

For the avoidance of doubt, the non-woven sheets are pressed (under heating) in a direction parallel to their thinnest dimension. Non-woven sheets will typically have two dimensions which are much larger than the third dimension, and the sheets are pressed parallel to this third dimension. Where two or more non-woven sheets are provided and pressed, the two or more non-woven sheets are stacked one on top of the other so that they substantially overlap and the smallest dimension of each non-woven sheet is aligned. This forms a stack of sheets which is subsequently heated and pressed. The sheets in the stack overlap with one another and the smallest dimension of each non-woven sheet is aligned.

Typically, pressing the polymer nanofibres or non-woven sheets involves subjecting them to a pressure of from 0.01 to 5 MPa, more typically from 0.05 to 3 MPa, for instance from 0.1 to 1 MPa. Suitable pressures for use in the process of the present invention are typically greater than 1 kPa, preferably greater than 5 kPa, in some circumstances greater than 10 kPa. Typically, pressures of no more than 500 kPa are used, preferably no more than 200 kPa, more preferably no greater than 150 kPa, for instance no greater than 100 kPa, 50 kPa or 30 kPa. Suitable pressure ranges may be, for instance, from 1 to 500 kPa, from 5 to 200 kPa, from 5 to 150 kPa, from 5 to 100 kPa from 5 to 50 kPa, or from 10 to 30 kPa. Pressure may be applied by any suitable means. For instance, pressure may be applied using a manual press or hydraulic press. The pressure applied may be varied to alter the physical properties of the media. Generally, a higher pressure will result in a more robust medium, having a lower porosity and lower thickness. A lower pressure tends to yield a comparatively less robust medium, with a higher porosity and higher thickness. Thicker chromatography media may be preferred when it is desirable to maximise the binding properties.

The length of time for which the polymer nanofibres or non-woven sheets are pressed is not particularly restricted, and typical pressing times may be determined by one of skill in the art. Where the one or more polymer nanofibres or one or more non-woven sheets are heated and pressed simultaneously, this is typically carried out for from 1 to 30 minutes, preferably from 1 to 10 minutes, more preferably from 3 to 7 minutes, even more preferably for around 5 minutes.

Heating the one or more polymer nanofibres or one or more non-woven sheets may be effected by conventional means, for example using an oven. Where the one or more polymer nanofibres or one or more non-woven sheets are heated and pressed simultaneously, heating may be effected by a heated press or by placing the one or more polymer nanofibres or one or more non-woven sheets between weights, for example metal sheets, in a heated oven.

The stack of non-woven sheets is heated and pressed to fuse points of contact between the nanofibres of adjacent sheets.

Where two or more non-woven sheets, each comprising one or more nanofibres, are stacked one on top of the other and subjected to conditions of heat and pressure, sections of a polymer nanofibre in a sheet may be in contact with sections of the same nanofibre, and/or with sections of other nanofibres in the same non-woven sheet, and/or with sections of nanofibres in adjacent non-woven sheets. Sections of nanofibres in non-woven sheets are not typically in contact with sections of nanofibres in other non-woven sheets which are not adjacent.

Thus, heating and pressing a stack of two or more non-woven sheets may fuse points of contact between sections of a nanofibre in a sheet with other sections of the same nanofibre, and/or between sections of a nanofibre in a sheet with sections of another nanofibre (if present) in the same non-woven sheet, and/or or between sections of a nanofibre in a sheet with sections of a nanofibre in an adjacent non-woven sheet. Typically, simultaneously heating and pressing two or more non-woven sheets fuses points of contact between sections of a polymer nanofibre in a sheet with sections of a polymer nanofibre in an adjacent sheet. Preferably, simultaneously heating and pressing two or more non-woven sheets fuses points of contact between sections of a polymer nanofibre in a sheet with other sections of the same nanofibre, and fuses points of contact between sections of the polymer nanofibre in the sheet with sections of a polymer nanofibre in an adjacent sheet. More preferably, heating and pressing two or more non-woven sheets fuses points of contact between sections of a nanofibre in a sheet with other sections of the same nanofibre, and between sections of a nanofibre in a sheet with sections of another nanofibre (if present) in the same non-woven sheet, and/or between sections of a nanofibre with sections of a nanofibre in an adjacent non-woven sheet. Most preferably, heating and pressing two or more non-woven sheets fuses points of contact between sections of a nanofibre in a sheet with other sections of the same nanofibre, and between sections of the nanofibre in the sheet with sections of another nanofibre (if present) in the same non-woven sheet, and between sections of the nanofibre in the sheet with sections of a nanofibre in an adjacent non-woven sheet.

In a simple example where two non-woven sheets are provided, each non-woven sheet containing a single polymer nanofibre, heating and pressing the first and second non-woven sheets preferably fuses points of contact between sections of the polymer nanofibre in the first non-woven sheet with other sections of the polymer nanofibre in the first non-woven sheet, and between sections of the polymer nanofibre in the first non-woven sheet with sections of the polymer nanofibre in the second non-woven sheet, and typically also between sections of the polymer nanofibre in the second non-woven sheet with other sections of the polymer nanofibre in the second non-woven sheet.

Typically, the polymer nanofibres or non-woven sheets are heated to a temperature below the melting point of the polymer. Use of a higher temperature could result in destruction of the nanofibre structure. In some circumstances it is advantageous to use a temperature which is below the glass transition temperature of the polymer. In other circumstances a temperature above the glass transition temperature of the polymer may be used. The melting points and glass transition temperatures of polymers suitable for use in the claimed processes are well known to the skilled person.

Typically, the polymer nanofibres or non-woven sheets are heated to a temperature between a temperature at which points of contact between sections of the one or more polymer nanofibres begin to fuse and the melting point of the polymer. Preferably, the polymer nanofibres or non-woven sheets are heated to a temperature between a temperature at which points of contact between sections of the one or more polymer nanofibres begin to fuse and the glass transition temperature of the polymer.

Typically, a temperature of greater than 40° C., preferably 30° C., more preferably 20° C., below the melting point of the polymer is used. Typically, a temperature of not greater than 1° C., preferably 2° C., more preferably 5° C., below the melting point of the polymer is used. Thus, typically a temperature range is used from 40° C. below the melting point of the polymer to 1° C. below the melting point of the polymer, preferably from 30° C. below the melting point of the polymer to 2° C. below the melting point of the polymer, more preferably from 20° C. below the melting point of the polymer to 5° C. below the melting point of the polymer.

In the case where the polymer is cellulose acetate, the cellulose acetate nanofibres or non-woven sheets, each comprising one or more cellulose acetate nanofibres, are heated to or at a temperature between 190 to 220° C., preferably from 195 to 218° C., for instance from 195 to 215° C., 195 to 210° C., 190 to 210° C., 195 to 205° C. or 210 to 215° C. Other suitable temperature ranges which may be used include 200 to 220° C., preferably from 205 to 218° C., for instance from 205 to 210° C. or 210 to 215° C. Where the cellulose acetate nanofibres or non-woven cellulose acetate sheets are heated and pressed simultaneously, a temperature of between 190 to 220° C. is typically employed, for instance from 190 to 210° C., 195 to 218° C., 195 to 215° C., 195 to 210° C., 195 to 205° C., 210 to 215° C., 200 to 220° C., 205 to 218° C., or 205 to 210° C., in some circumstances around 207° C.

The polymer nanofibres or non-woven sheets are typically heated for from 1 to 120 minutes, for instance from 5 to 60 minutes. Where the polymer nanofibres or non-woven sheets are heated and pressed simultaneously, heating is typically carried out for from 1 to 30 minutes, preferably from 1 to 10 minutes, more preferably from 3 to 7 minutes, even more preferably for around 5 minutes.

Typically, the polymer nanofibres or non-woven sheets have an average pore size after pressing and heating, i.e. the resultant pressed and heated product, of from 0.1 to 1.0 µm, preferably from 0.3 to 0.9 µm, more preferably from 0.4 to 0.8 µm, even more preferably from 0.5 to 0.7 µm, yet more preferably from 0.6 to 0.7 µm, for example from 0.6 to 0.65 µm.

Typically, the polymer nanofibres or non-woven sheets have an average density after pressing and heating, i.e. the resultant pressed and heated product, of from 200 to 1000 kg/m$^3$, preferably 250 to 750 kg/m$^3$, more preferably from 350 to 650 kg/m$^3$, in some circumstances from 450 to 550 kg/m$^3$. Other preferable densities include from 200 to 750 kg/m$^3$, 200 to 650 kg/m$^3$, 200 to 550 kg/m$^3$, 250 to 750 kg/m$^3$, 250 to 650 kg/m$^3$, and 250 to 550 kg/m$^3$.

The polymer nanofibres or non-woven sheets are usually heated and pressed simultaneously. Some embodiments may involve pressing the polymer nanofibres or non-woven sheets then subsequently heating them; or heating the polymer nanofibres or non-woven sheets then subsequently pressing them. Where the polymer nanofibres or non-woven sheets are heated and pressed simultaneously, heating and pressing is typically carried out in a heated press or by placing the polymer nanofibres or non-woven sheets between weights, for example metal sheets, in a heated oven.

The process of the present invention may also involve wetting the polymer nanofibres or non-woven sheets prior to pressing and heating. Thus, the process may involve an additional step between steps (I) and (II) of wetting the stack of sheets. Alternatively, the process may involve forming a stack of wetted non-woven sheets in step (I). An optionally aqueous organic solvent is typically used to wet the polymer nanofibres/non-woven sheets/stack of sheets, preferably an aqueous organic solvent. Organic solvents are typically chosen so as not to dissolve the polymer nanofibres. A skilled person will be well aware of which solvents can be used so as not to dissolve polymer nanofibres. Alcohols are preferable as the organic solvent, for instance methanol, ethanol or isopropanol, preferably ethanol. Aqueous ethanol is preferred in some instances. Thus, some embodiments may involve wetting, following by heating and pressing simultaneously. Other embodiments may involve wetting, followed by pressing followed by heating. Yet further embodiments may involve wetting, followed by heating, followed by pressing.

Typically, the pressed and heated polymer nanofibres or sheets, i.e. the pressed and heated product, have a thickness of 0.05 to 10 mm, for instance 0.1 to 5 mm.

In some embodiments, the process of the present invention comprises providing one or more polymer nanofibres, pressing the one or more polymer nanofibres and heating the one or more polymer nanofibres to fuse points of contact between sections of the one or more polymer nanofibres. Preferably, the process of the present invention comprises providing one or more non-woven sheets, each comprising one or more polymer nanofibres, pressing the one or more non-woven sheets and heating the one or more non-woven sheets to fuse points of contact between sections of the one or more polymer nanofibres. Fusion of points of contact between sections of the one or more polymer nanofibres refers to the one or more polymer nanofibres contained in the one or more non-woven sheets.

In some embodiments, the process of the present invention involves wetting as defined herein and pressing a stack of two or more non-woven sheets as defined herein, followed by subsequent heating as defined herein. Typical wetting, pressing and heating conditions are as defined above. Thus in this embodiment, the present invention provides a process for preparing a functionalised polymeric chromatography medium, which process comprises (I) providing two or more non-woven sheets as defined herein stacked one on top of the other, each said sheet comprising one or more polymer nanofibres as defined herein, (II) wetting the stack of sheets with an optionally aqueous organic solvent as defined herein, (III) pressing the stack of sheets as defined herein, (IV) heating the pressed stack to fuse points of contact between the nanofibres of adjacent sheets as defined herein, and (V) contacting the wetted, pressed and heated product with a reagent as defined herein which functionalises the product of step (II) as a chromatography medium as defined herein.

Chemical Modification of Nanofibres

The processes of the present invention typically involve chemical modification of the one or more polymer nanofibres or one or more non-woven sheets to functionalise them for use in chromatography. In its simplest form this involves contacting the one or more polymer nanofibres or one or more non-woven sheets (which may have been pressed and heated) with a reagent to functionalise the product as a chromatography medium.

Optionally, prior to this step of contacting with a reagent, the one or more polymer nanofibres or one or more non-woven sheets (which may have been pressed and heated) may be treated to deprotect or activate any functional groups on the polymer.

Deprotection of the functional groups is typically effected so that the functional groups can react with the reagent. For instance, when the polymer is cellulose, typically one or more cellulose acetate nanofibres or non-woven sheets, each comprising one or more cellulose acetate nanofibres, is provided and, prior to contacting with a reagent, the cellulose acetate is treated to convert it to cellulose. This involves the deprotection of acetylated hydroxyl groups to give hydroxyl groups. Conversion of cellulose acetate to cellulose is typically effected using aqueous alkali, preferably NaOH in water:ethanol, more preferably water:ethanol 2:1, for a period of greater than 12 hrs, for example from 12 to 36 hours. This step typically takes place after the one or more cellulose acetate nanofibres or non-woven sheets, each comprising one or more cellulose acetate nanofibres, has been pressed and heated. Alternatively, this step may be carried out before the one or more cellulose acetate nanofibres or non-woven sheets, each comprising one or more cellulose acetate nanofibres, has been pressed and heated. Activation of functional groups is discussed further below.

The reagent typically functionalises the chromatography medium by introducing one or more moieties which render the functionalised product comprising the one or more moieties suitable for use as a chromatography medium. The one or more moieties introduced will depend on the particular chromatography technique for which the medium is to be used. Suitable moieties and reagents are discussed further below. Typically, the reagent reacts with one or more functional groups present on the one or more polymer nanofibres, typically contained within the one or more non-woven sheets, to create the one or more moieties. Typical functional groups include hydroxyl, amino and carboxy groups. Thus, typically one or more hydroxyl, amino and/or carboxy groups are functionalised in the process of the present invention.

Although the present invention envisages processes involving only a single treatment with a reagent, processes involving multiple functionalising steps are preferred. Such processes may lead to products with improved binding properties.

Thus, typically, functionalisation by contacting with a reagent is effected by contacting in a batchwise fashion two or more times with a reagent. Batchwise functionalisation means that the polymer nanofibre material (which has been optionally pressed, heated, deprotected and/or activated) is reacted with a reagent to functionalise it, that reaction is then stopped and the resultant (partially) functionalised material reacted with a separate batch of reagent. Reacting in a batchwise fashion does not simply refer to adding more portions of reagent to a reaction vessel, for instance.

Batchwise functionalisation is typically carried out from two to ten times, i.e. 2, 3, 4, 5, 6, 7, 8, 9 or 10 times. Preferably batchwise funtionalisation is carried out between two and four times.

Each step of contacting with a reagent in a batchwise fashion typically comprises (a) contacting with the reagent, (b) isolating the product of step (a) from the reagent, (c) optionally treating the product of step (b) with aqueous alkali, and (d) optionally washing the product of step (b)/(c) with water. Preferably, each step of contacting with a reagent in a batchwise fashion comprises (a) contacting with the reagent, (b) isolating the product of step (a) from the reagent, (c) treating the product of step (b) with aqueous alkali, and (d) optionally washing the product of step (b)/(c) with water. More preferably, each step of contacting with a reagent in a batchwise fashion comprises (a) contacting with the reagent, (b) isolating the product of step (a) from the reagent, (c) treating the product of step (b) with aqueous alkali, and (d) washing the product of step (b)/(c) with water.

The steps of treating with aqueous alkali typically employ hot aqueous alkali, i.e. between 70 and 90° C. Alternatively, the step of treating with aqueous alkali may be carried out at room temperature.

The reagent used in each step of contacting with a reagent in a batchwise fashion may be the same or different, but is preferably the same.

In circumstances where between two and four steps of contacting with a reagent in a batchwise fashion are employed, the one or more polymer nanofibres or one or more non-woven sheets, each comprising one or more polymer nanofibres, which may have been pressed, heated and/or deprotected, are typically treated by (1) (a1) contacting with the reagent, (b1) isolating the product of step (a1) from the reagent, (c1) optionally treating the product of step (b1) with aqueous alkali, and (d1) optionally washing the product of step (b1) (c1) with water, and
(2) (a2) contacting the product of step (b1)/(c1)/(d1) with the reagent, (b2) isolating the product of step (a2) from the reagent, (c2) optionally treating the product of step (b2) with aqueous alkali, and (d2) optionally washing the product of step (b2)/(c2) with water; or (1) (a1) contacting with the reagent, (b1) isolating the product of step (a1) from the reagent, (c1) optionally treating the product of step (b1) with aqueous alkali, and (d1) optionally washing the product of step (b1) (c1) with water,
(2) (a2) contacting the product of step (b1)/(c1)/(d1) with the reagent, (b2) isolating the product of step (a2) from the reagent, (c2) optionally treating the product of step (b2) with aqueous alkali, and (d2) optionally washing the product of step (b2/(c2) with water, and
(3) (a3) contacting the product of step (b2)/(c2)/(d2) with the reagent, (b3) isolating the product of step (a3) from the reagent, (c3) optionally treating the product of step (b3) with aqueous alkali, and (d3) optionally washing the product of step (b3)/(c3) with water; or (1) (a1) contacting with the reagent, (b1) isolating the product of step (a1) from the reagent, (c1) optionally treating the product of step (b1) with aqueous alkali, and (d1) optionally washing the product of step (b1) (c1) with water,
(2) (a2) contacting the product of step (b1)(c1)/(d1) with the reagent, (b2) isolating the product of step (a2) from the reagent, (c2) optionally treating the product of step (b2) with aqueous alkali, and (d2) optionally washing the product of step (b2)/(c2) with water,
(3) (a3) contacting the product of step (b2)/(c2)/(d2) with the reagent, (b3) isolating the product of step (a3) from the reagent, (c3) optionally treating the product of step (b3) with aqueous alkali, and (d3) optionally washing the product of step (b3)/(c3) with water, and
(4) (a4) contacting the product of step (b3)/(c3)/0(d3) with the reagent, (b4) isolating the product of step (a4) from the reagent, (c4) optionally treating the product of step (b4) with aqueous alkali, and (d4) optionally washing the product of step (b4)/(c4) with water.

Typically, each step of contacting with a reagent in a batchwise fashion comprises treating with the reagent for between 1 and 20 minutes.

In certain circumstances, contacting with a reagent may comprise placing one or more polymer nanofibres or one or more non-woven sheets, each comprising one or more polymer nanofibres, which may have been pressed, heated, deprotected and/or activated (i.e. the polymer material) in a holder, and causing a reagent to flow through the holder so that the reagent flows in contact with the polymer material which functionalises the polymer material as a chromatography medium. Functionalising polymer material in this manner may in certain circumstances be more efficient than simply contacting the polymer material with the reagent, in a flask or beaker for example.

Typically, the holder is a filter holder adapted to hold the polymer material. Typically, the filter holder holds the polymer material such that an aqueous or liquid substance which is passed through the filter holder flows in contact with the polymer material. Thus, in the context of the present invention, the filter holder preferably holds the polymer material such that a reagent which is caused to flow through the filter holder flows in contact with the polymer material.

Typically, the reagent is caused to flow through the holder under pressure.

Typically, the reagent is caused to flow through the holder using a pump, preferably an HPLC pump.

Typically, the reagent is caused to flow through the holder in a cyclical manner. Thus, any reagent exiting the holder is recycled and passed through the holder one of more further times.

Typically, the reagent is caused to flow through the holder for a period of time from 1 to 20 minutes.

Typically, the reagent is caused to flow through the holder at a rate of 10 to 100 mL/min.

Typically, after the reagent has been caused to flow through the holder the resultant product is treated with aqueous alkali, and optionally washed with water. Preferably, after the reagent has been caused to flow through the holder the resultant product is treated with aqueous alkali, and washed with water. Treatment with aqueous alkali is preferably treatment with hot aqueous alkali as defined above. Typically, after the reagent has been caused to flow through the holder the resultant product is removed from the holder prior to any further treatment steps. Thus, preferably, after the reagent has been caused to flow through the holder the resultant product is removed from the holder, treated with aqueous alkali, and optionally washed with water. More preferably, after the reagent has been caused to flow through the holder the resultant product is removed from the holder, treated with aqueous alkali, and washed with water.

The reagent functionalises the product of the preceding physical and chemical processing steps to yield a chromatography medium, specifically a functionalised chromatography medium. Typically, the reagent functionalises the product of the preceding steps so that it is suitable for use in an ion exchange, affinity capture or hydrophobic chromatography method. Thus, contacting with the reagent typically yields a chromatography medium which is functionalised with one or more moieties which are negatively charged, one or more moieties which are positively charged, one or more proteins, mimetic or synthetic ligands that mimic the action of protein ligands, peptides, antibodies or fragments thereof, dyes, histidine, groups containing a metal cation, or hydrophobic groups. Examples of such groups are defined further below. Suitable reagents for introducing such groups will be evident to the skilled person. 2-chloro-N,N-diethylamine hydrochloride (DEACH) and glycidyltrimethylammonium are preferred as the reagent, particularly when the functionalised chromatography medium is for use in an anion exchange chromatography method. Other preferred reagents are TEMPO followed by sodium perchlorate, or allyl glycidyl ether followed by sodium disulphite, particularly when the funtionalised chromatography medium is for use in a cation exchange chromatography method. Another preferred reagent is NaIO$_4$ followed by Protein A, particularly when the functionalised chromatography medium is for use in an affinity chromatography method. Another preferred reagent is styrene oxide, particularly when the functionalised chromatography medium is for use in a hydrophobic chromatography method.

Chromatography Media and Methods

The products of the process of the present invention are functionalised chromatography media, i.e. chromatography media that have been modified chemically to render them suitable for use in one or more chromatography methods. Specific chemical modifications are discussed in more detail below. In general terms, such chemical modification changes the chemical and/or physical properties of the chromatography medium. This in turn affects how the chromatography medium behaves when used in a chromatography method. The modifications may, for example, change the polarity, hydrophobicity or biological binding properties of the functionalised chromatography medium compared to its unfunctionalised form. The modifications may, in certain circumstances, change more than one of the polarity, hydrophobicity or biological binding properties of the functionalised chromatography medium compared to its unfunctionalised form. In one embodiment, the modification changes the polarity and hydrophobicity of the functionalised chromatography medium compared to its unfunctionalised form.

The chromatography media are typically in the form of membranes. Such membranes are suitable for use in membrane chromatography methods. Membrane chromatography methods are well known to the person skilled in the art and are discussed in "Membrane Processes in Biotechnologies and Pharmaceutics" ed. Catherine Charcosset, Elsevier, 2012, the entirety of which is incorporated herein by reference.

Typically, the functionalised polymer chromatography media are suitable for use in chromatography methods chosen from ion exchange chromatography, affinity capture chromatography, hydrophobic chromatography and mixed mode chromatography. In certain circumstances, the chromatography method operates in "mixed mode", i.e. utilising more than one form of interaction, i.e. ion exchange, affinity capture and hydrophobic interaction. Typically, such "mixed mode" chromatography involves ion exchange (ionic) and hydrophobic interactions. Preferably, the functionalised polymer chromatography media are suitable for use in chromatography methods chosen from ion exchange chromatography, affinity capture chromatography, and hydrophobic chromatography. In operation, such chromatography methods involve passing a mobile phase containing desired molecule over an adsorbent phase, here the functionalised chromatography media. The adsorbent phase is typically chosen such that the desired molecule is retained on it in preference to other components also present in the mobile phase.

Typically, the polymer chromatography medium is functionalised with DEAE, Q, SP, CM, Protein A, phenyl, or MEP groups, for instance DEAE or CM groups. Generally, the polymer is cellulose and the chromatography medium is functionalised with DEAE, Q, SP, CM, Protein A, phenyl, or MEP groups, for instance DEAE or CM groups. Thus, the functionalised chromatography medium may be cellulose derivatised with DEAE, Q, SP, CM, Protein A, phenyl, or MEP groups, for instance DEAE or CM groups.

Ion exchange chromatography is a technique for separating molecules, typically ions or polar molecules, based on their ionic charge. Functionalised chromatography media for use in such methods therefore contain one or more moieties which are positively or negatively charged. Positive and/or negative charges in functionalised chromatography media are usually balanced with one or more counter ions. Ion exchange chromatography involves one or more of cation exchange chromatography and anion exchange chromatography.

Functionalised chromatography media for use in cation exchange chromatography contain one or more moieties which are negatively charged. Typical negatively charged moieties include one or more carboxylate, sulphonate or phosphonate groups, or mixtures thereof, i.e. the moieties typically contain one or more —COO$^-$, —SO$_3^-$, or —P(OH)$_2$O$^-$ groups, or mixtures thereof. Typical functionalised chromatography media for use in cation exchange chromatography contain one or more —O—CH$_2$COO$^-$, —CH$_2$COO$^-$, —SO$_3^-$, —CH$_2$CH$_2$CH$_2$SO$_3^-$, —CH$_2$CH$_2$SO$_3^-$, or —P(OH)$_2$O$^-$ moieties.

Functionalised chromatography media for use in anion exchange chromatography contain one or more moieties which are positively charged. Typical positively charged moieties include one or more quaternary amine groups. Typical functionalised chromatography media for use in anion exchange chromatography contain one or more —N$^+$(CH$_3$)$_3$, —N$^+$(C$_2$H$_5$)H, —CH$_2$CH$_2$N$^+$(C$_2$H$_5$)H, —CH$_2$CH$_2$N(C$_2$H$_5$)$_2$(CH$_2$CH(OH)CH$_3$), —O—CH$_2$CH$_2$—N$^+$(CH$_3$)$_3$, —CH$_2$CH$_2$N$^+$(CH$_3$)$_3$, or —CH$_2$CH$_2$N$^+$(CH$_3$)$_2$H moieties.

Affinity capture chromatography is a technique for separating molecules based on their affinity to particular ligands, usually but not always biological ligands. This method may, for example, rely on the attractive forces between antibodies and antigens or enzymes and substrates. Functionalised chromatography media for use in affinity capture chromatography typically contain one or more moieties chosen from one or more proteins, peptides, antibodies or fragments thereof, dyes, histidine, or groups containing a metal cation. Alternatively, functionalised chromatography media for use in affinity capture chromatography may contain mimetic or synthetic ligands that mimic the action of protein ligands.

Typical proteins for use in affinity capture chromatography are well known to the person skilled in the art and include Protein A, Protein G and Protein L.

Typical antibodies and fragments thereof for use in affinity capture chromatography are well known to the person skilled in the art and include IgG.

Typical dyes for use in affinity capture chromatography are well known to the person skilled in the art and include Yellow HE-4R, Red HE-3B and Cibacron Blue F3G.

Typical groups containing metal cations for use in affinity capture chromatography are well known to the person skilled in the art. Such groups typically contain a chelating agent to immobilize metal cations. The metal cation is typically chosen from copper, nickel, zinc and cobalt cations, preferably Cu$^{2+}$, Ni$^{2+}$, Zn$^{2+}$ and Co$^{2+}$.

Hydrophobic interaction chromatography is a technique for separating molecules based on their hydrophobicity. Functionalised chromatography media for use in such methods therefore contain one or more moieties which contain one or more hydrophobic groups. Typical hydrophobic groups include propyl, butyl, phenyl, and octyl groups.

Mixed mode (or multimodal) chromatography is a technique for separating molecules based on two or more characteristics, typically hydrophobicity and ionic charge. This may involve a combination of hydrophobicity and anionic properties, or a combination of hydrophobicity and cationic properties. Functionalised chromatography media for use in such methods therefore typically contain one or more moieties which are positively or negatively charged, typically as defined above, and which contain one or more hydrophobic groups, typically as defined above. Positive and/or negative charges in functionalised chromatography media are usually balanced with one or more counter ions. Functionalised chromatography media for use in such methods may also contain one or more hydrophobic groups which are ionisable, for use in so-called Hydrophobic Charge Induction Chromatography (HCIC). Thus, in one embodiment, mixed mode chromatography is Hydrophobic Charge Induction Chromatography. Suitable groups for use in such methods are 4-mercapto-ethyl-pyridine (MEP) groups and octylamine groups.

Functionalised chromatography media for use in mixed mode chromatography methods which involve a combination of hydrophobic and anionic interactions contain one or more moieties which are positively charged, typically as defined above, and one or more hydrophobic groups, typically as defined above. Suitable groups for use in such methods are N-benzyl methyl ethanolamine groups and N-benzoyl-homocysteine groups. Functionalised chromatography media for use in mixed mode chromatography methods which involve a combination of hydrophobic and cationic interactions contain one or more moieties which are negatively charged, typically as defined above, and one or more hydrophobic groups, typically as defined above. Suitable groups for use in such methods are N-benzoyl-homocysteine groups.

The processes claimed in the present invention for preparing functionalised chromatography media typically involve introducing one or more moieties into a chromatography medium such that the resultant functionalised product comprising the one or more moieties is suitable for use as a chromatography medium in a chromatography method. Typical moieties, media, reagents and methods are as defined above. The one or more moieties are introduced by reacting a reagent with one or more functional groups contained on the one or more polymer nanofibres or one or more non-woven sheets, each comprising one or more polymer nanofibres, which have typically been pressed, heated, deprotected and/or activated. Typical functional groups include hydroxyl, amino and carboxyl groups.

The one or more functional groups may be activated prior to reaction with a reagent. Conventional activation methods known in the art may be employed. Thus, in the case where the functional group is an hydroxyl group, such a group may be activated by treating with carbonyl diimidazole (CDI), bisoxiranes, cyanuric acid, N-hydroxy succinimide esters (NHS) or 2-fluoro-1-methyl pyridinium toluene-4 sulphonate (FMP). In the case where the functional group is an amino group, such a group may be activated by treating with epichlorohydrine, glutaraldehyde or epoxide. In the case where the functional group is a carboxyl group, such a group may be activated by treating with CDI or 1-ethyl-3-(3-dimethylaminopropyl)carbodiimide (EDC).

A skilled person can choose suitable reagents to introduce particular moieties into particular polymers, for example on the basis of the functional groups contained in those polymers. Typical reagents include 2-chloro-N,N-diethylamine hydrochloride (DEACH).

Typically,
the chromatography method is a cationic exchange method, and the reagent functionalises the chromatography medium with a carboxylate, sulphonate or phosphonate group;
the chromatography method is an anionic exchange method, and the reagent functionalises the chromatography medium with a quaternary amino or diethylamine group;
the chromatography method is an affinity capture chromatography method, and the reagent functionalises the chromatography medium with a protein, peptide, antibody or fragment thereof, dye, histidine, or group containing a metal cation;
the chromatography method is a hydrophobic interaction chromatography method, and the reagent functionalises the chromatography medium with a propyl, butyl, phenyl, or octyl group; or
the chromatography method is a mixed mode chromatography method, and the reagent functionalises the chromatography medium with a MEP, octylamine, N-benzyl methyl ethanolamine or N-benzoyl-homocysteine group.

Preferably,

- the chromatography method is a cationic exchange method, and the reagent functionalises the chromatography medium with a carboxylate, sulphonate or phosphonate group;
- the chromatography method is an anionic exchange method, and the reagent functionalises the chromatography medium with a quaternary amino or diethylamine group;
- the chromatography method is an affinity capture chromatography method, and the reagent functionalises the chromatography medium with a protein, peptide, antibody or fragment thereof, dye, histidine, or group containing a metal cation; or
- the chromatography method is a hydrophobic interaction chromatography method, and the reagent functionalises the chromatography medium with a propyl, butyl, phenyl, or octyl group; or Particular Embodiments of the Process of the Invention In its broadest sense, the present invention provides processes for preparing functionalised chromatography media, which process involves treating one or more polymer nanofibres with a combination of physical and chemical processing steps to yield a functionalised product that is suitable for use as a chromatography medium in a chromatography method.

Typically, the one or more polymer nanofibres are as defined herein. The one or more polymer nanofibres may be provided as one or more non-woven sheets, each comprising one or more polymer nanofibres. Typically, two or more non-woven sheets are provided, each comprising one or more polymer nanofibres.

Typically, the physical processing steps are the steps of heating and pressing as defined herein. Typically, the steps of heating and pressing are carried out simultaneously.

Typically, the chemical processing steps are the steps of contacting with a reagent as defined herein.

Typically, the chromatography method is as defined herein.

The present invention typically provides a process for preparing a functionalised polymeric chromatography medium, which process comprises (I) providing two or more non-woven sheets as defined herein, stacked one on top of the other and each comprising one or more polymer nanofibres as defined herein, (II) simultaneously heating and pressing the stack of sheets to fuse points of contact between the nanofibres of adjacent sheets as defined herein, and (III) contacting the pressed and heated product with a reagent as defined herein which functionalises the product of step (II) as a chromatography medium as defined herein.

In a preferred embodiment of the invention, the step of functionalising with a reagent is carried out in a batchwise fashion. This increases the binding capacity of the resultant functionalised polymeric chromatography medium. Thus, in this preferred embodiment, the present invention provides a process for preparing a functionalised polymeric chromatography medium, which process comprises (I) providing two or more non-woven sheets as defined herein, stacked one on top of the other and each comprising one or more polymer nanofibres as defined herein, (II) simultaneously heating and pressing the stack of sheets to fuse points of contact between the nanofibres of adjacent sheets as defined herein, and (III) contacting the product of step (II) in a batchwise fashion at least two times with a reagent as defined herein which functionalises the product of step (II) as a chromatography medium as defined herein.

In a further preferred embodiment of the invention, the step of functionalising with a reagent is carried out by convective flow. Such a process is typically more efficient than a standard diffusive process. Thus, in this further preferred embodiment, the present invention provides a process for preparing a functionalised polymeric chromatography medium, which process comprises (I) providing two or more non-woven sheets as defined herein, stacked one on top of the other and each comprising one or more polymer nanofibres as defined herein, (II) simultaneously heating and pressing the stack of sheets to fuse points of contact between the nanofibres of adjacent sheets as defined herein, and (III) placing the product of step (II) in a holder as defined herein, and (IV) causing a reagent as defined herein to flow through the holder so that the reagent flows in contact with the product of step (II) which functionalises the product of step (II) as a chromatography medium as defined herein.

It is preferred that the functionalised polymer chromatography medium is a functionalised cellulose chromatography medium.

In a more preferred embodiment of the invention, the present invention provides a process for preparing a functionalised cellulose chromatography medium, which process comprises (i) providing two or more non-woven sheets as defined herein, stacked one on top of the other and each comprising one or more cellulose acetate nanofibres as defined herein, (ii) simultaneously heating and pressing the stack of sheets to fuse points of contact between the cellulose acetate nanofibres of adjacent sheets as defined herein, (iii) treating the pressed and heated product to convert the cellulose acetate to cellulose as defined herein, and (iv) contacting the thus-obtained product with a reagent as defined herein which functionalises the product of step (iii) as a chromatography medium as defined herein.

In a most preferred embodiment of the invention, the present invention provides a process for preparing a functionalised cellulose chromatography medium, which process comprises (i) providing two or more non-woven sheets as defined herein, stacked one on top of the other and each comprising one or more cellulose acetate nanofibres as defined herein, (ii) simultaneously heating and pressing the stack of sheets to fuse points of contact between the cellulose acetate nanofibres of adjacent layers as defined herein, (iii) treating the pressed and heated product to convert the cellulose acetate to cellulose as defined herein, and (iv) contacting the thus-obtained product in a batchwise fashion between two and four times with a reagent as defined herein which functionalises the product of step (iii) as a chromatography medium as defined herein.

In a further most preferred embodiment of the invention, the present invention provides a process for preparing a functionalised cellulose chromatography medium, which process comprises (i) providing two or more non-woven sheets as defined herein, stacked one on top of the other and each comprising one or more cellulose acetate nanofibres as defined herein, (ii) simultaneously heating and pressing the stack of sheets to fuse points of contact between the cellulose acetate nanofibres of adjacent sheets as defined herein, (iii) treating the pressed and heated product to convert the cellulose acetate to cellulose as defined herein, (iv) placing the thus-obtained product in a holder as defined herein, and (v) causing a reagent as defined herein to flow through the holder so that the reagent flows in contact with the product obtained in step (iii) which functionalises the product of step (iii) as a chromatography medium as defined herein.

It is preferred that between two and thirty, more preferably between five and twenty five said sheets are stacked one on top of the other in step (I), each sheet comprising 1, 2 or 3 polymer nanofibers and each sheet having a thickness of from 5 to 40 μm.

It is also preferred in step (II) that the stack of sheets be simultaneously heated at a temperature below the melting point of the polymer and pressed under a pressure of from 0.01 to 5 MPa for 1 to 120 minutes to fuse points of contact between the nanofibres of adjacent sheets, the resultant pressed and heated product having an average density of 250 to 750 kg/m³ and a thickness of 0.05 to 10 mm.

It is more preferred that:
  between two and thirty, more preferably between five and twenty five said sheets are stacked one on top of the other in step (I), each sheet comprising 1, 2 or 3 polymer nanofibers and each sheet having a thickness of from 5 to 40 μm; and
  in step (II) that the stack of sheets be simultaneously heated at a temperature below the melting point of the polymer and pressed under a pressure of from 0.01 to 5 MPa for 1 to 120 minutes to fuse points of contact between the nanofibres of adjacent sheets, the resultant pressed and heated product having an average density of 250 to 750 kg/m³ and a thickness of 0.05 to 10 mm.

It is preferred that between two and thirty, more preferably between five and twenty five said sheets are stacked one on top of the other in step (I), each sheet consisting of a single polymer nanofibre, and each sheet having a thickness of from 5 to 120 m and an area density of from 1 to 40 g/m².

It is also preferred in step (II) that the stack of sheets are simultaneously heated at a temperature below the melting point of the polymer and pressed under a pressure of from 1 to 500 kPa for 1 to 30 minutes to fuse points of contact between the nanofibres of adjacent sheets, the resultant pressed and heated product having an average density of 200 to 1000 kg/m³ and a thickness of 0.05 to 10 mm.

It is more preferred that:
  between two and thirty, more preferably between five and twenty five said sheets are stacked one on top of the other in step (I), each sheet consisting of a single polymer nanofibre, and each sheet having a thickness of from 5 to 120 μm and an area density of from 1 to 40 g/m²; and
  in step (II) that the stack of sheets are simultaneously heated at a temperature below the melting point of the polymer and pressed under a pressure of from 1 to 500 kPa for 1 to 30 minutes to fuse points of contact between the nanofibres of adjacent sheets, the resultant pressed and heated product having an average density of 200 to 1000 kg/m³ and a thickness of 0.05 to 10 mm.

In a preferred embodiment, the one or more polymer nanofibres are pressed and heated. This improves the structural properties of the resultant functionalised polymeric chromatography medium. Thus, in this preferred embodiment the present invention provides a process for preparing a functionalised polymeric chromatography medium, which process comprises (I) providing one or more polymer nanofibres as defined herein, (II) pressing the one or more polymer nanofibres as defined herein, (III) heating the one or more polymer nanofibres to fuse points of contact between sections of the one or more polymer nanofibres as defined herein, and (IV) contacting the pressed and heated product with a reagent as defined herein which functionalises the product of step (III) as a chromatography medium as defined herein.

In this preferred embodiment, the step of providing one or more polymer nanofibres typically comprises providing one or more non-woven sheets, each comprising one or more polymer nanofibres.

In a further preferred embodiment, the step of functionalising with a reagent is carried out in a batchwise fashion. This increases the binding capacity of the resultant functionalised polymeric chromatography medium. Thus, in this further preferred embodiment, the present invention provides a process for preparing a functionalised polymeric chromatography medium, which process comprises (I) providing one or more polymer nanofibres as defined herein, (II) optionally pressing the one or more polymer nanofibres as defined herein, (III) optionally heating the one or more polymer nanofibres to fuse points of contact between sections of the one or more polymer nanofibres as defined herein, and (IV) contacting the product of step (I), (II) or (III) in a batchwise fashion at least two times with a reagent as defined herein which functionalises the product of step (I), (II) or (III) as a chromatography medium as defined herein.

In this further preferred embodiment, the step of providing one or more polymer nanofibres typically comprises providing one or more non-woven sheets, each comprising one or more polymer nanofibres.

This further preferred embodiment preferably comprises (I) providing one or more polymer nanofibres as defined herein, (II) pressing the one or more polymer nanofibres as defined herein, (III) heating the one or more polymer nanofibres to fuse points of contact between sections of the one or more polymer nanofibres as defined herein, and (IV) contacting the product of step (II) in a batchwise fashion at least two times with a reagent as defined herein which functionalises the product of step (III) as a chromatography medium as defined herein.

This further preferred embodiment more preferably comprises (I) providing one or more non-woven sheets, each comprising one or more polymer nanofibres as defined herein, (II) pressing the one or more non-woven sheets as defined herein, (III) heating the one or more non-woven sheets to fuse points of contact between sections of the one or more polymer nanofibres as defined herein, and (IV) contacting the product of step (III) in a batchwise fashion at least two times with a reagent as defined herein which functionalises the product of step (III) as a chromatography medium as defined herein.

In a yet further preferred embodiment, the step of functionalising with a reagent is carried out by convective flow. Such a process is typically more efficient than a standard diffusive process. Thus, in this further preferred embodiment, the present invention provides a process for preparing a functionalised polymeric chromatography medium, which process comprises (I) providing one or more polymer nanofibres as defined herein, (II) optionally pressing the one or more polymer nanofibres as defined herein, (III) optionally heating the one or more polymer nanofibres to fuse points of contact between sections of the one or more polymer nanofibres as defined herein, (IV) placing the product of step (I), (II) or (III) in a holder as defined herein, and (V) causing a reagent as defined herein to flow through the holder so that the reagent flows in contact with the product of step (I), (II) or (III) which functionalises the product of step (I), (II) or (III) as a chromatography medium as defined herein.

This yet further preferred embodiment preferably comprises (I) providing one or more polymer nanofibres as defined herein, (II) pressing the one or more polymer nanofibres as defined herein, (III) heating the one or more polymer nanofibres to fuse points of contact between sections of the one or more polymer nanofibres as defined herein, (IV) placing the product of step (III) in a holder as defined herein, and (V) causing a reagent as defined herein to flow through the holder so that the reagent flows in contact with the product of step (III) which functionalises the product of step (III) as a chromatography medium as defined herein.

This yet further preferred embodiment more preferably comprises (I) providing one or more non-woven sheets, each comprising one or more polymer nanofibres as defined herein, (II) pressing the one or more non-woven sheets as defined herein, (III) heating the one or more non-woven sheets to fuse points of contact between sections of the one or more polymer nanofibres as defined herein, (IV) placing the product of step (III) in a holder as defined herein, and (V) causing a reagent as defined herein to flow through the holder so that the reagent flows in contact with the product of step (III) which functionalises the product of step (III) as a chromatography medium as defined herein.

It is preferred that the functionalised polymer chromatography medium is a functionalised cellulose chromatography medium.

In a most preferred embodiment, the present invention provides a process for preparing a functionalised cellulose chromatography medium, which process comprises (i) providing one or more non-woven sheets as defined herein, each comprising one or more cellulose acetate nanofibres as defined herein, (ii) pressing the one or more non-woven sheets as defined herein, (iii) heating the one or more non-woven sheets to fuse points of contact between sections of the one or more cellulose acetate nanofibres as defined herein, (iv) treating the pressed and heated product to convert the cellulose acetate to cellulose as defined herein, and (v) contacting the thus-obtained product in a batchwise fashion between two and four times with a reagent as defined herein which functionalises the product of step (iv) as a chromatography medium as defined herein.

In a further most preferred embodiment, the present invention provides a process for preparing a functionalised cellulose chromatography medium, which process comprises (i) providing one or more non-woven sheets as defined herein, each comprising one or more cellulose acetate nanofibres as defined herein, (ii) pressing the one or more non-woven sheets as defined herein, (iii) heating the one or more non-woven sheets to fuse points of contact between sections of the one or more cellulose acetate nanofibres as defined herein, (iv) treating the pressed and heated product to convert the cellulose acetate to cellulose as defined herein, (v) placing the thus-obtained product in a holder as defined herein, and (vi) causing a reagent as defined herein to flow through the holder so that the reagent flows in contact with the product obtained in step (iv) which functionalises the product of step (iv) as a chromatography medium as defined herein.

Functionalised Chromatography Medium of the Invention

The present invention also provides a functionalised chromatography medium which is obtainable by the process of the present invention.

Also provided is provides a functionalised chromatography medium which is obtained by the process of the present invention.

The functionalised chromatography medium of the present invention typically has a porosity of from 0.1 to 1.0 μm, preferably from 0.3 to 0.9 μm, more preferably from 0.4 to 0.8 μm, even more preferably from 0.5 to 0.7 μm, yet more preferably from 0.6 to 0.7 μm, for example from 0.6 to 0.65 μm.

The functionalised chromatography medium of the present invention has a density of from 200 to 1000 kg/m$^3$, preferably 250 to 750 kg/m$^3$, more preferably from 350 to 650 kg/m$^3$, in some circumstances from 450 to 550 kg/m$^3$. Other preferable densities include from 200 to 750 kg/m$^3$, 200 to 650 kg/m$^3$, 200 to 550 kg/m$^3$, 250 to 750 kg/m$^3$, 250 to 650 kg/m$^3$, and 250 to 550 kg/m$^3$.

Typically, the functionalised chromatography medium of the present invention has a thickness of 0.05 to 10 mm, for instance 0.1 to 5 mm.

Preferably, the functionalised chromatography medium of the present invention is functionalised so that it is suitable for use in a chromatography method as defined herein, for instance ion exchange chromatography, affinity capture chromatography and hydrophobic chromatography.

The functionalised chromatography medium of the present invention is typically in the form of a membrane.

Chromatography Cartridge of the Invention

The present invention also provides a chromatography cartridge. The chromatography cartridge of the present invention comprises one or more functionalised chromatography media of the present invention. Alternatively, the chromatography cartridge of the present invention is obtainable by carrying out the process of the present invention and incorporating the thus-obtained product into a cartridge.

Also provided is a process for preparing a chromatography cartridge which comprises carrying out the process of the present invention and incorporating the thus-obtained product into a cartridge.

The chromatography cartridge is typically suitable for use in chromatography, preferably a chromatography method as defined herein.

A chromatography cartridge of the present invention typically comprises one or more functionalised chromatography media of the present invention within a holder, for example a holder as defined above. The holder is typically cylindrical.

Typically, the chromatography cartridge comprises one or more functionalised chromatography media of the present invention stacked inside a cylindrical holder.

Typically, the chromatography cartridge comprises two or more functionalised chromatography media of the present invention. Typically, the chromatography cartridge comprises up to twenty functionalised chromatography media of the present invention.

Typically, the chromatography cartridge also comprises one or more frits within the typically cylindrical holder. Frits are well known to the person skilled in the art and refer to rigid porous structures, typically rigid metal, polymeric or ceramic, preferably rigid metal or ceramic, porous structures. Frits are typically included in a chromatography cartridge to improve flow distribution through the cartridge and/or to support the one or more functionalised chromatography media of the present invention. Pores in typical frits have diameters from 1 to 1000 μm, preferably from 5 to 500 μm, more preferably from 10 to 150 μm. Other suitable frit pore diameters include from 1 to 20 μm, preferably from 5 to 10 μm, more preferably from 3 to 7 μm.

Typically, the chromatography cartridge also comprises one or more inlet fluid distribution means and/or outlet fluid collection means. Such means are well known to the person skilled in the art.

Chromatography Method of the Invention

The present invention also provides use of a functionalised chromatography medium of the invention or a chromatography cartridge of the invention in chromatography, particularly in a chromatography method as defined herein.

The present invention also provides a process for isolating one or more biological molecules from a mobile phase, which process comprises contacting one or more biological molecules in a mobile phase with a functionalised chromatography medium of the invention or a chromatography cartridge of the invention. The chromatography medium or chromatography cartridge binds preferentially to the one or more biological molecules in the mobile phase, typically in preference to other components (for instance other biological molecules) also present in the mobile phase. This can be carried out in accordance with conventional methods known for the bind phase of such chromatographic methods.

Thus, typically, this chromatographic process is an ion (anion or cation) exchange, affinity capture, hydrophobic interaction or mixed mode chromatography process.

Preferably, the chromatographic process is an anion exchange chromatography process and the chromatography medium is functionalised with DEAE or Q; the chromatographic process is a cation exchange chromatography process and the chromatography medium is functionalised with SP or CM; the chromatographic process is an affinity capture chromatography process and the chromatography medium is functionalised with Protein A; or the chromatographic process is a hydrophobic interaction chromatography process and the chromatography medium is functionalised with phenyl groups.

Thus, the present invention provides a chromatography process which comprises the above step. Typically, the chromatography process is carried out in accordance with a chromatography method as defined above.

The chromatography process typically comprises a further step of recovering the one or more biological molecules from the functionalised chromatography medium or chromatography cartridge. This step can typically be effected by contacting the functionalised chromatography medium or chromatography cartridge to which is adsorbed the one or more biological molecules with an elution buffer. This can be carried out in accordance with conventional methods known for the elute phase of such chromatographic methods. Thus, the process is typically a bind-elute chromatographic method.

Between the bind and elute steps, the process may further comprise a step of washing the functionalised chromatography medium or chromatography cartridge of the invention to which is adsorbed the one or more biological molecules. This washing step is carried out to remove any components which are not bound to the functionalised chromatography medium or chromatography cartridge. This can be carried out in accordance with conventional methods known for the washing phase of such chromatographic methods.

After the elute step, the process may further comprise a step of regenerating the functionalised chromatography medium or chromatography cartridge of the invention. Typically this is effected by contacting the functionalised chromatography medium or chromatography cartridge from which the one or more biological molecules have been eluted with a buffer. This can be carried out in accordance with conventional methods known for the regeneration phase of such chromatographic methods.

Typically, the one or more biological molecules are chosen from proteins, polypeptides, antibodies, amino acids, viruses and nucleic acids, including, for example, recombinant proteins, monoclonal antibodies, viral vaccines and plasmid DNA.

The monoclonal antibody may be a multispecific antibody (e.g. a bispecific antibody) or a domain-deleted antibody. Preferably the monoclonal antibody is a humanized antibody or a human antibody. Antigen-binding fragments of monoclonal antibodies may be used. Examples of antibody fragments include Fab, Fab', $F(ab')_2$ and Fv fragments, diabodies and single chain antibodies.

Typically, the chromatographic process employs a simulated or actual moving bed system. Thus typically, the process comprises introducing the one or more biological molecules in a mobile phase into one or more simulated or actual moving bed chromatography apparatuses having a plurality of linked chromatography columns, which chromatography columns contain as adsorbent the functionalised chromatography medium of the present invention.

Any known simulated or actual moving bed apparatus may be used to carry out the chromatographic process, provided that it comprises, as adsorbent, the functionalised chromatography medium of the present invention.

Simulated and actual moving bed chromatography are known techniques, familiar to those of skill in the art. The principle of operation involves countercurrent movement of a liquid eluent phase and a solid adsorbent phase. This operation allows minimal usage of solvent making the process economically viable. Such separation technology has found applications in diverse areas including purification of biological molecules using membrane adsorbents.

A simulated moving bed system consists of a number of individual columns containing adsorbent which are connected together in series. Eluent is passed through the columns in a first direction. The injection points of the feedstock and the eluent, and the separated component collection points in the system are periodically shifted by means of a series of valves. The overall effect is to simulate the operation of a single column containing a moving bed of the solid adsorbent. Thus, a simulated moving bed system consists of columns which, as in a conventional stationary bed system, contain stationary beds of solid adsorbent through which eluent is passed, but in a simulated moving bed system the operation is such as to simulate a continuous countercurrent moving bed.

An actual moving bed system is similar in operation to a simulated moving bed system. However, rather than shifting the injection points of the feed mixture and the eluent, and the separated component collection points by means of a system of valves, instead a series of adsorption units (i.e. columns) are physically moved relative to the feed and drawoff points. Again, operation is such as to simulate a continuous countercurrent moving bed.

Polymeric Medium of the Invention

The present invention also provides a process for preparing a polymeric medium, which process comprises providing two or more non-woven sheets stacked one on top of the other as defined herein, each said sheet comprising two or more polymer nanofibres as defined herein, and simultaneously heating and pressing the stack of sheets to fuse points of contact between the nanofibres of adjacent sheets as defined herein. Also provided is a polymeric medium obtainable by that process.

The first step of the process involves providing a stack of two or more non-woven sheets. Thus, the present invention also provides a process for preparing a polymeric medium, which process comprises providing a stack of two or more non-woven sheets as defined herein, each said sheet comprising two or more polymer nanofibres as defined herein, and simultaneously heating and pressing the stack of sheets to fuse points of contact between the nanofibres of adjacent sheets as defined herein. Also provided is a polymeric medium obtainable by that process.

This process may also involve wetting as defined herein and pressing a stack of two. or more non-woven sheets as defined herein, followed by subsequent heating as defined herein. Typical wetting, pressing and heating conditions are as defined above. Thus in this embodiment, the present invention provides a process for preparing a polymeric medium, which process comprises (I) providing two or more non-woven sheets as defined herein stacked one on top of the other, each said sheet comprising one or more polymer nanofibres as defined herein, (II) wetting the stack of sheets with an optionally aqueous organic solvent as defined herein, (III) pressing the stack of sheets as defined herein, and (IV) heating the pressed stack to fuse points of contact between the nanofibres of adjacent sheets as defined herein.

Preferred features for the polymeric medium of the invention and the process for producing that polymeric medium are as defined above for the chromatography medium of the invention and the process used to produce the chromatography medium.

The following Examples illustrate the invention.

Materials and Equipment

The following materials, equipment and techniques were employed unless stated otherwise BSA protein Bovine Albumin Serum Fraction V, ≥96% with molecular weight of ~66 kDa and all other chemicals were purchased from Sigma-Aldrich Co. (Sigma-Aldrich Company Ltd. Dorset, UK) of the highest purity available and used without further purification, unless stated otherwise.

Cytochrome c, from Equine Heart, ≥90% with molecular weight of ~12 kDA was purchased from Merck Chemical (Merck Serono Ltd. Middlesex, UK).

Preparative Example 1

Nanofibre Membrane Preparation

A 0.20 g/mL solution of cellulose acetate, with a relative molecular mass of 29,000 g/mol, was dissolved in acetone/dimethylformamide/ethanol (2:2:1). Electrospinning was carried out in a Climate Zone climate control cabinet (a1-safetech Luton, UK) to allow temperature and humidity control of the ambient conditions. Optimized conditions from O. Hardick, et al, J. Mater. Sci. 46 (2011) 3890 were used to produce non-woven sheets of electrospun cellulose acetate nanofibres with low distribution of fibre diameters, average thicknesses of 20 microns and average area densities of 10 $g/m^2$.

Once electrospun, fifteen non-woven sheets of nanofibres with a face surface area of 100 $cm^2$ were stacked one on top of the other and pressed in a manual hydraulic press at a pressure of 1 MPa for two minutes. After pressing, the sheet of material was immediately placed in a pre-heated oven at 213° C. for 5 minutes between metal sheets. The pressure between the metal sheets was determined as 20 kPa. The pressed and heated material was then cut into multiple 25 mm diameter discs.

Example 1

Chemical Modification by Convection

A cellulose acetate nanofibre disc was prepared as above and modified chemically to yield anion exchange surface functionality. A disc having a thickness of 0.188 mm and total volume 0.1 mL was modified as set out below.

The nanofibre disc was packed into a filter holder prior to derivatisation. Deacetylation was carried out using 30 mL of 0.1 M NaOH in DI water:ethanol (2:1), which was pumped through the disc in a cyclical manner using a Dionex, P680 HPLC pump at a rate of 25 mL/min for 24 hours. The disc was then rinsed with 300 mL DI H2O at a rate of 25 mL/min. Anion-exchange surface functionality was then imparted by cycling 20 mL warm (40° C.) 15% 2-chloro-N,N-diethylethylamine hydrochloride 99% (DEACH) aqueous solution through the disc at 40 mL/min for 10 min. The disc was then removed from the filter holder housing and left for 30 seconds to drip dry before placing into 20 mL hot (80° C.) 0.5 M NaOH in a 50 mL sample tube on a shaker table with gentle agitation for 10 min. Finally the disc was rinsed in multiple volumes of DI H2O and left to dry before use.

Example 2

An experiment was carried out as set out in Example 1 above, except that the cellulose acetate nanofibre disc used had a thickness of 0376 mm and total volume 0.2 mL.

Example 3

Chemical Modification by Diffusion

A cellulose acetate nanofibre disc was prepared as above. A disc having a thickness of 0.188 mm and total volume 0.1 mL was modified as set out below.

The disc was placed in a 50 mL sample tube containing 30 mL 0.1M NaOH in DI water:ethanol (2:1) for 24 hours on a laboratory shaker table to deacetylate the cellulose acetate to form regenerated cellulose. The disc was then rinsed thoroughly in 10×30 mL volumes of DI water for 5 minutes each on the shaker table. Anion-exchange surface functionality was then introduced by placing the rinsed disc into a sample tube with 20 mL warm (40° C.) 15% 2-chloro-N,N diethylethylamine hydrochloride 99% (DEACH) aqueous solution for 10 min. The adsorbent was removed and allowed to drip dry for 30 seconds before being placed in 20 mL hot (80° C.) 0.5M NaOH in a new sample tube on the shaker table for 10 min. Finally the disc was rinsed in multiple volumes of DI H2O and left to dry before use.

Example 4

An experiment was carried out as set out in Example 1 above, except that the cellulose acetate nanofibre disc used had a thickness of 0.376 mm and total volume 0.2 mL.

Example 5

Analysis of Bioseparation Performance

Nanofibre discs prepared and modified in accordance with Examples 1 to 4 were analysed to compare the protein binding performance of equivalent mass and volume nanofibre membranes derivatised by the two different methods. This was to determine the extent of the modification of the surface area presented by these nanofibre systems.

Experiments were conducted using an AKTA Basic (GE Healthcare Life Sciences, Buckinghamshire, UK) with online measurement of UV absorbance (280 nm), pH, and conductivity.

Nanofibre discs prepared and modified in accordance with Examples 1 to 4 were equilibrated with 5 mL 20 mM Bis-Tris, pH 5.3 wash buffer at a rate of 480 cm/h and then loaded with 1 mL of a two component protein solution containing 1 mg/mL BSA and 0.25 mg/mL Cytochrome C. 5 mL wash buffer was then passed through the adsorbent before 5 mL 0.4M NaCl 20 mM Bis-Tris, pH 5.3 elution buffer was introduced. The eluted capacity was then analysed using Unicorn 5.0 software as measured by the integration of the peak area.

A mixture of BSA and Cytochrome C was used to take advantage of their different isoelectric points and therefore suitability for separation by ion-exchange chromatography. Cytochrome C has a pI of 10.0 while BSA has a pI of 4.7 in water at 25° C. This means that in a Bis-Tris buffer solution at pH 5.3 the Cytochrome C will have a net positive charge and will not bind to the weak anion exchange surface of the DEAE adsorbent. In contrast, at this pH above the pI of BSA, BSA will have a net negative surface charge and therefore will bind to the DEAE adsorbent. As the salt concentration is increased during elution the interaction between the negative surface charge of the BSA and the anion exchanger is out-competed by the salt ions and so the BSA is removed from the adsorbent and collected.

The performance of the adsorbent was analysed over a number of operational cycles to determine reproducibility with regard to the lifetime of the adsorbents. The Table below sets out the average binding capacities for the discs tested.

| Sample | Thickness of adsorbent (mm) | Volume of adsorbent (mL) | Binding capacity (mg/mL) |
| --- | --- | --- | --- |
| Example 1 | 0.188 | 0.1 | 5.64 ± 0.10 |
| Example 3 | 0.188 | 0.1 | 5.56 ± 0.40 |
| Example 2 | 0.376 | 0.2 | 6.46 ± 0.44 |
| Example 4 | 0.376 | 0.2 | 5.88 ± 0.56 |

For both thicknesses of nanofibre discs, the convective modification process gave a higher binding capacity than the diffusive modification process. This effect was more pronounced for the thicker disc.

The ability of chemical reagents to reach functional surfaces of the polymer system was also observed to depend on the thickness of the nanofibre membrane. Thus, for the thicker nanofibre membranes tested there was a significantly improved binding capacity observed for the DEAE nanofibre adsorbents that were derivatised through convective flow. This suggests that for protocols investigated, diffusion is insufficient for the chemical reagents to reach all binding surface areas.

Example 6

Repeated Diffusive Chemical Modification

Anion-exchange surface derivatisation of cellulose nanofibre discs was carried out as described above in Example 4, i.e. using a cellulose acetate nanofibre disc having a thickness of 0.376 mm and total volume 0.2 mL. The chemical modification was then repeated from the point of DEACH introduction to the end of the protocol.

Thus, the disc obtained in Example 4 was placed into a sample tube with 20 mL warm (40° C.) 15% 2-chloro-N,N-diethylethylamine hydrochloride 99% (DEACH) aqueous solution for 10 min. The adsorbent was removed and allowed to drip dry for 30 seconds before being placed in 20 mL hot (80° C.) 0.5M NaOH in a new sample tube on a shaker table for 10 min, then rinsed in multiple volumes of DI H2O.

Example 7

An experiment was carried out as in Example 6, except that the chemical modification was repeated a further time.

Thus, the disc obtained in Example 6 was placed into a sample tube with 20 mL warm (40° C.) 15% 2-chloro-N,N-diethylethylamine hydrochloride 99% (DEACH) aqueous solution for 10 min. The adsorbent was removed and allowed to drip dry for 30 seconds before being placed in 20 mL hot (80° C.) 0.5M NaOH in a new sample tube on a shaker table for 10 min, then rinsed in multiple volumes of DI H2O.

Example 8

An experiment was carried out as in Example 7, except that the chemical modification was repeated a further time.

Thus, the disc obtained in Example 7 was placed into a sample tube with 20 mL warm (40° C.) 15% 2-chloro-N,N-diethylethylamine hydrochloride 99% (DEACH) aqueous solution for 10 min. The adsorbent was removed and allowed to drip dry for 30 seconds before being placed in 20 mL hot (80° C.) 0.5M NaOH in a new sample tube on a shaker table for 10 min, then rinsed in multiple volumes of DI H2O.

Example 9

Discs produced in Examples 4 and 6 to 8 were analysed for binding capacity using the protocol set out above in Example 5. The pressure drop for each disc was also determined.

The Table below sets out the average binding capacities and pressure drops for the discs tested.

| Sample | Chemical modifications | Pressure drop (MPa) | Binding capacity (mg/mL) |
| --- | --- | --- | --- |
| Example 4 | x1 | 0.210 | 5.88 ± 0.56 |
| Example 6 | x2 | 0.205 | 13.31 ± 3.11 |
| Example 7 | x3 | 0.245 | 14.88 ± 0.38 |
| Example 8 | x4 | 0.205 | 15.88 ± 0.73 |

These results show a clear improvement in functional group substitution with repeated derivatisation protocol steps. Overall a 270% improvement in binding capacity was observed for the adsorbents tested using repeated protocol steps during derivatisation. Pressure drop was not affected by the repeated modification.

Structural stability of the repeat derivatisation DEAE nanofibre adsorbents did not appear to be affected and this was confirmed by reproducibility studies which showed constant performance over 50 cycles of typical operation.

FIG. 1 shows the flowthrough of cytochrome C+ unbound BSA as the first peak during loading of a 2-component mixture and the elution of BSA as the second peak. The average result for 50 equivalent binding runs is plotted ±1 standard deviation of the sample population (shown by dashed curves around the main curve of the same colour). These results show the reproducibility over the 50 equivalent binding runs and show that for the conditions chosen the nanofibre adsorbents performed reproducibly, capturing and eluting 99% of the BSA loaded. The standard deviation was calculated to show that the nanofibre adsorbent operates consistently.

Figure 2:
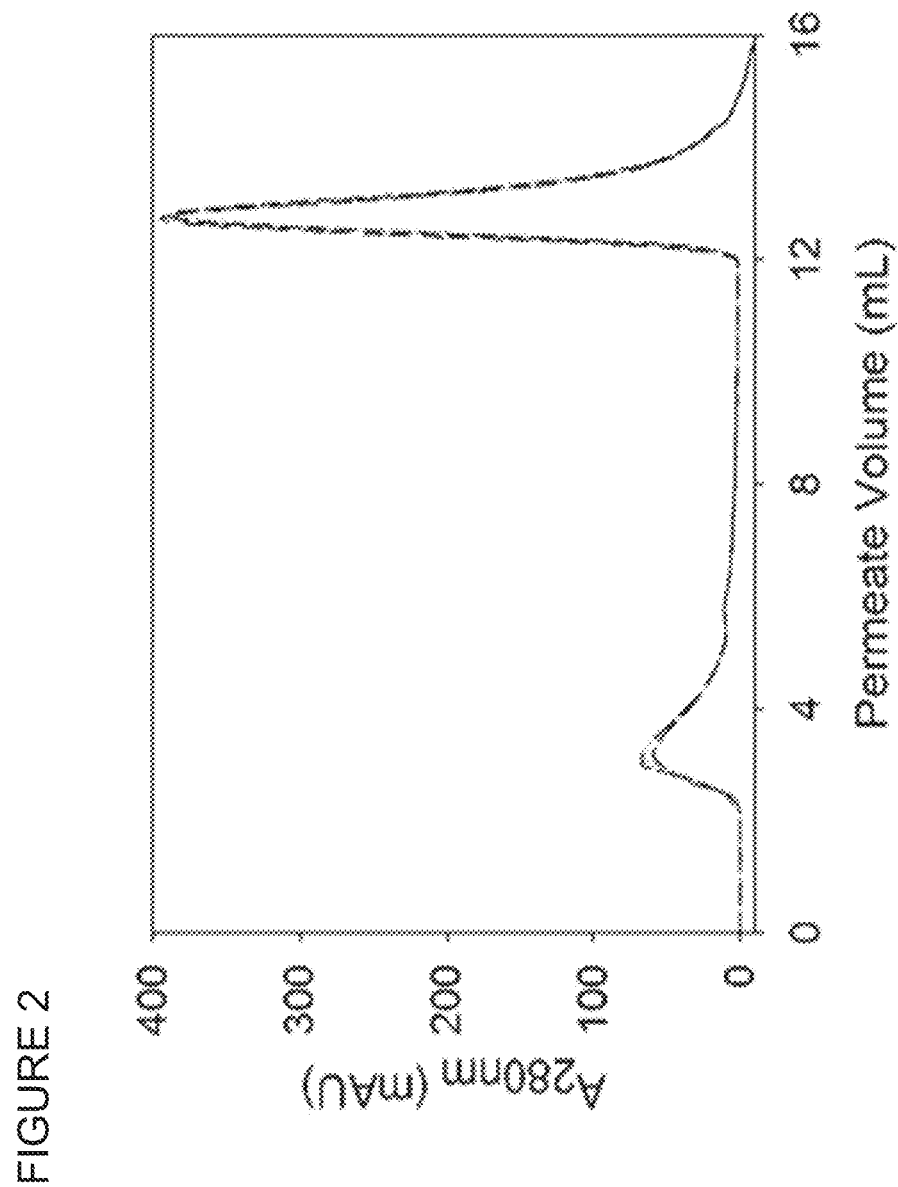
FIG. 2 shows the performance of a functionalised chromatography medium of the invention in anion exchange chromatography.

FIG. 2 shows the flowthrough of cytochrome C+unbound BSA as the first peak during loading of a 2-component mixture and the elution of BSA as the second peak. Multiple binding runs were carried out, and curves plotted for runs recorded 500 runs apart. The curves recorded for the two runs almost completely overlap. This also demonstrates the excellent reproducibility obtained with membranes prepared in accordance with the present invention. This is in contrast with the significant drop-off in performance after multiple runs reported with prior art membranes.

Preparative Example 2

A 0.20 g/mL solution of cellulose acetate, with a relative molecular mass of 29,000 g/mol, was dissolved in common solvents, e.g. acetone/dimethylformamide/ethanol. Optimized conditions from O. Hardick, et al, J. Mater. Sci. 46 (2011) 3890 were used to produce non-woven sheets of electrospun cellulose acetate nanofibres with low distribution of fibre diameters, average thicknesses of 20 microns and average area densities of 20 g/m$^2$.

Once electrospun, ten non-woven sheets of nanofibres with a face surface area of 100 cm$^2$ were stacked one on top of the other and placed in a pre-heated oven at 208° C. for 30 minutes between metal sheets. The pressure between the metal sheets was determined as 20 kPa. The pressed and heated material was then cut into multiple 25 mm diameter discs.

Analytical Example 1

Effect of Heating and Pressing

Ten sheets of cellulose acetate nanofibres were obtained as described in Preparative Example 2. The sheets were stacked one on top of the other and subjected to 20 kPa of pressure in a heated press whilst simultaneously being heated to 207° C. The stacked sheets were pressed and heated in the press for 5 minutes. After pressing and heating a disc of the resultant membrane was cut. The cellulose acetate fibres were deacetylated to cellulose using the method outlined in Example 3. Samples prepared in this way are referred to below as the "press" samples, reflecting that fact that heating was carried out in a heated press.

A "press" disc was placed in a rubber O-ring within a 50 ml syringe, as vessel to hold the O-ring in place. A weight in the form of a 10 ml pipette tip (mass 5.81 g) was placed into the centre of the nanofibre disc. A solution of 1 M NaOH was added to the vessel and a timer was used to determine the point of failure. The failure point was determined as the moment the pipette tip fell through the disc. The length of time taken for the pipette tip to fall through the disc indicates the chemical resistivity of the disc. This experiment was repeated three times.

This experimental set-up is shown in FIG. 3.

Further nanofibre discs were produced as described above, except that the ten nanofibre sheets were first pressed in a press (without heating) at a pressure of 20 kPa for one hour, followed by heating (without pressing) in an oven for five minutes at 207° C. Samples prepared in this way are referred to below as the "oven" samples, reflecting the fact that heating was carried out in an oven.

An "oven" disc was placed in a rubber O-ring and subjected to the chemical resistivity test described above. Again, this was repeated three times.

The results for the "press" and "oven" discs are set out in the Table below.

|  | Disc 1 | Disc 2 | Disc 3 |
| --- | --- | --- | --- |
| Oven | 66 minutes | 71 minutes | 88 minutes |
| Press | >120 hrs | >120 hrs | >120 hrs |

It can be seen from these results that discs that are pressed and heated simultaneously have superior chemical resistivity to those which are pressed (without heating) and subsequently heated (without pressing).

The "oven" disc showed discolouration and pitting within 10 minutes of exposure to 1M NaOH. The "press" disc showed little degradation even after 120 hours of exposure. Photographs of the respective discs are shown as FIG. 4.

Figure 5:
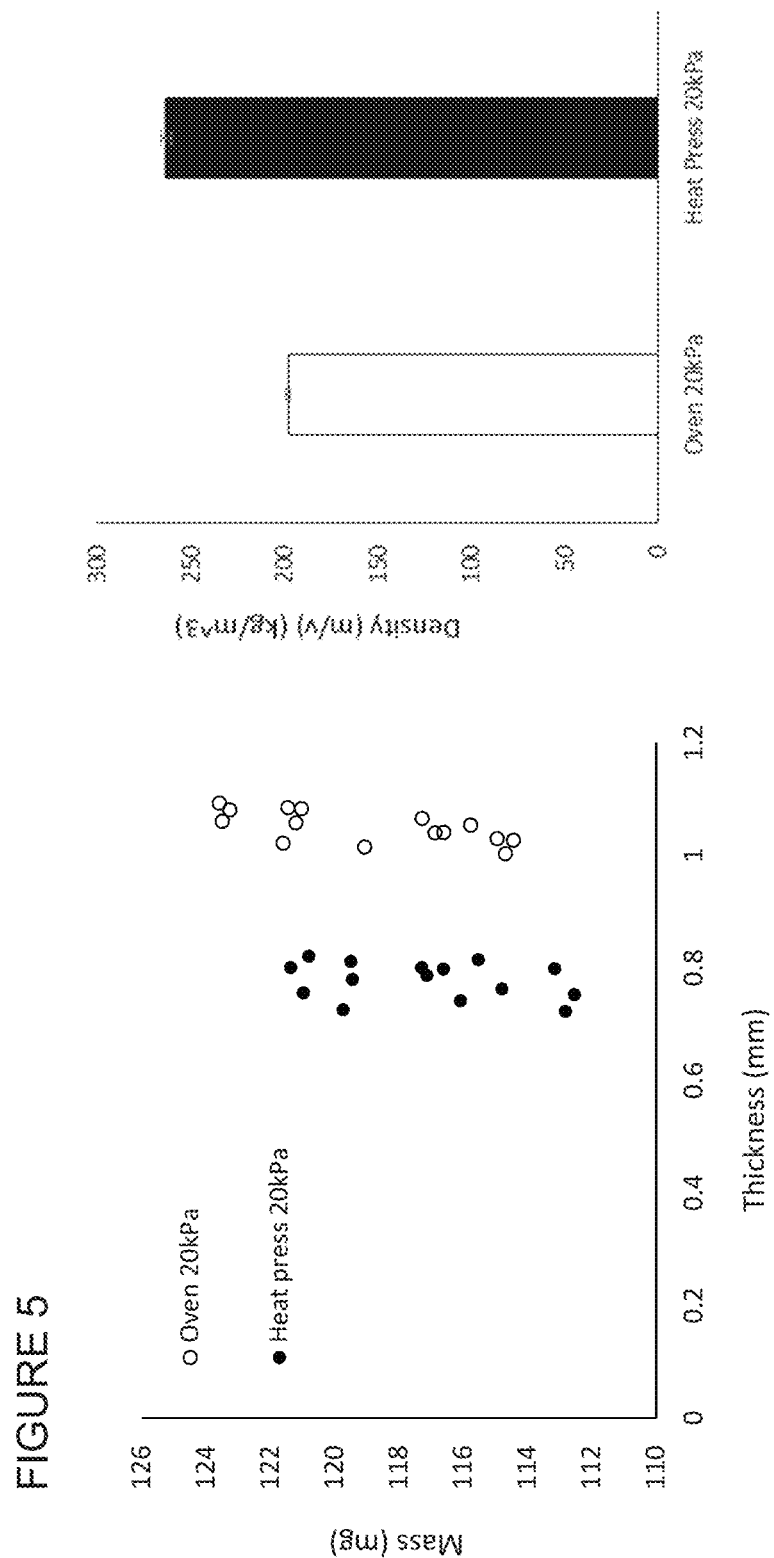
FIG. 5 shows the thickness and densities of membranes not in accordance with the invention and membranes in accordance with the invention.

The thickness and density of a number of "press" and "oven" discs were determined. The thicknesses and average densities of these discs are shown in FIG. 5. The "press" discs were found to be both thinner and denser than the "oven" discs.

Figure 6:
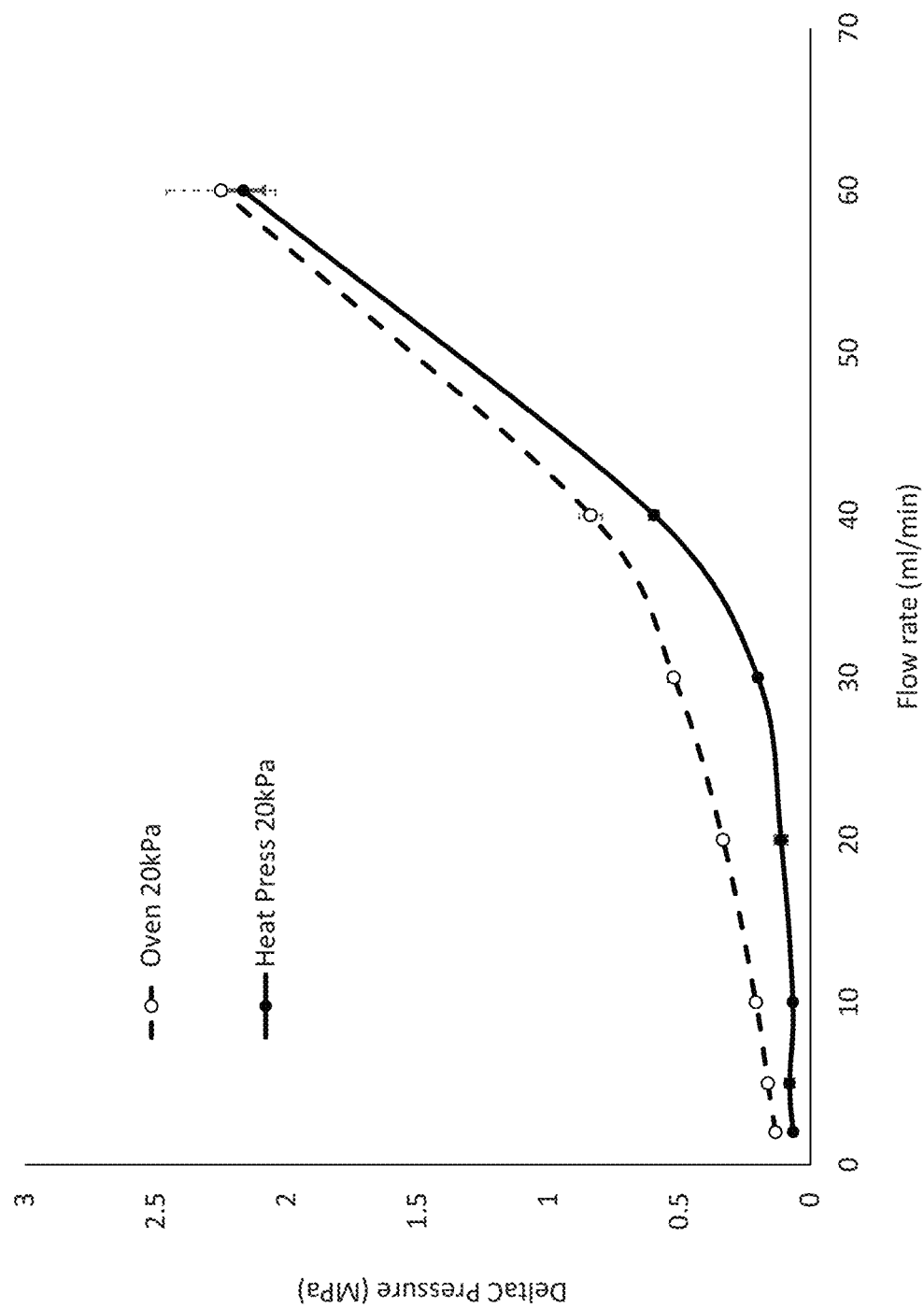
FIG. 6 shows the flow properties of membranes not in accordance with the invention and membranes in accordance with the invention.

The flow characteristics of "press" and "oven" discs were analysed by determining the delta column pressure drop at increasing flow rates (2, 5, 10, 20, 30, 40, 60 ml/min) of Tris-HCl buffer (pH 8) through the discs. The data obtained is shown as FIG. 6. It can be seen that the "press" and "oven" discs have similar flow characteristics.

Analytical Example 2

Effect of Varying Pressure

Regenerated cellulose discs were prepared using the method described in Analytical Example 1 for the "press" discs. Discs prepared in this manner are referred to below as the "20 kPa" discs.

Further discs were prepared using the method described above for the "20 kPa" discs, except that a pressure of 200 kPa was used instead of 20 kPa. Discs prepared in this manner are referred to below as the "200 kPa" discs.

Figure 7:
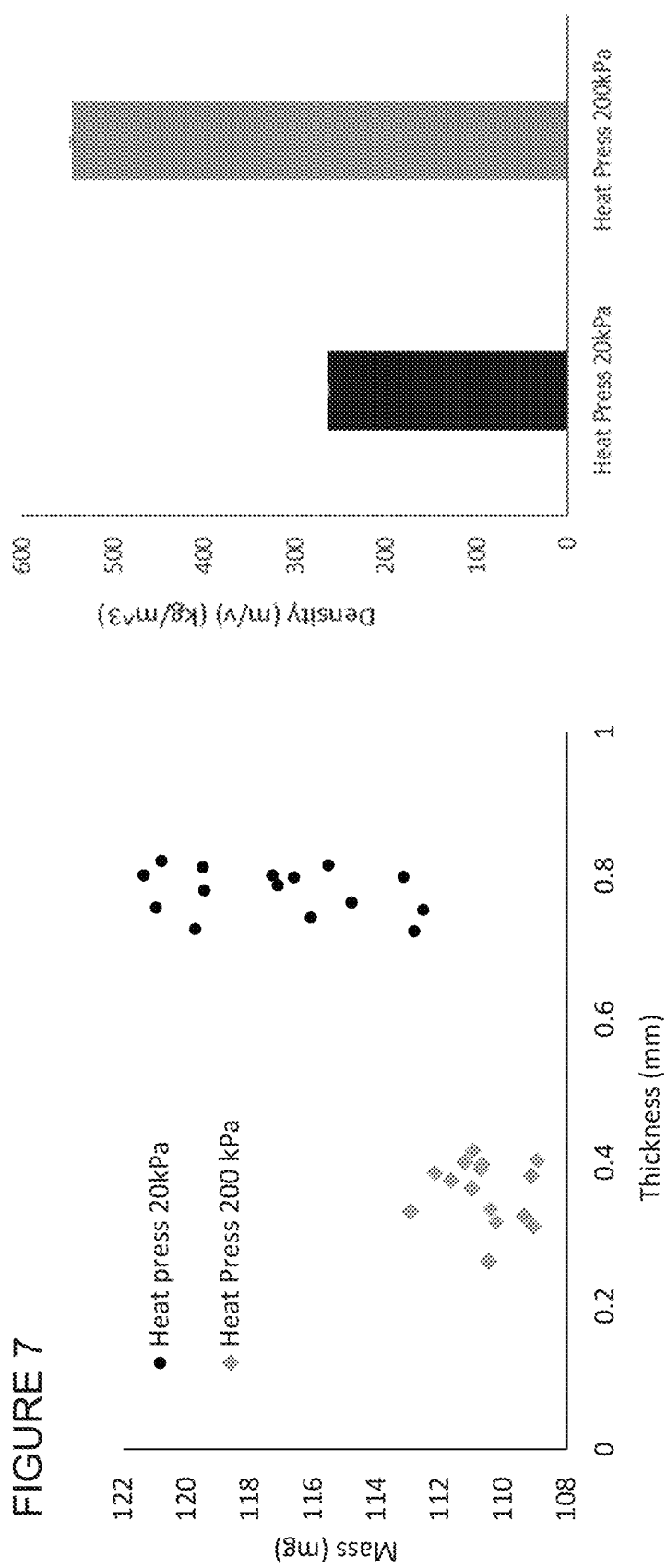
FIG. 7 shows the effect of pressure on the thickness and densities of membranes in accordance with the invention.

The thickness and density of a number of "20 kPa" and "200 kPa" discs were determined. The thicknesses and average densities of these discs are shown in FIG. 7. The "200 kPa" discs were found to be both thinner and denser than the "20 kPa" discs.

Figure 8:
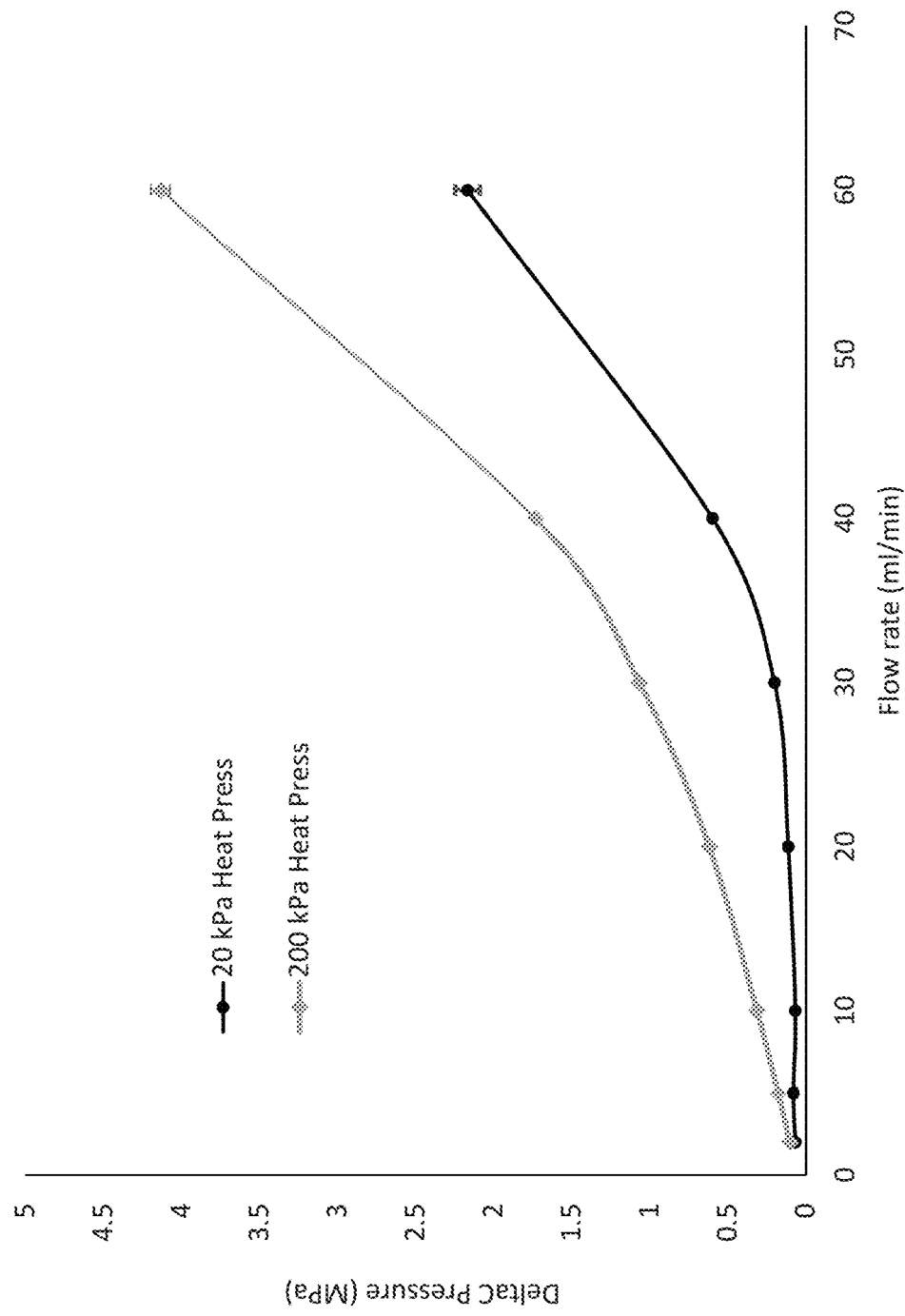
FIG. 8 shows the effect of pressure on the flow properties of membranes in accordance with the invention.

The flow characteristics of "2 kPa" and "200 kPa" discs were analysed using the method described in Analytical Example 1. The data obtained is shown as FIG. 8. It can be seen that the pressure drop over the "200 kPa" discs is higher than that over the "20 kPa" discs.

Figure 9:
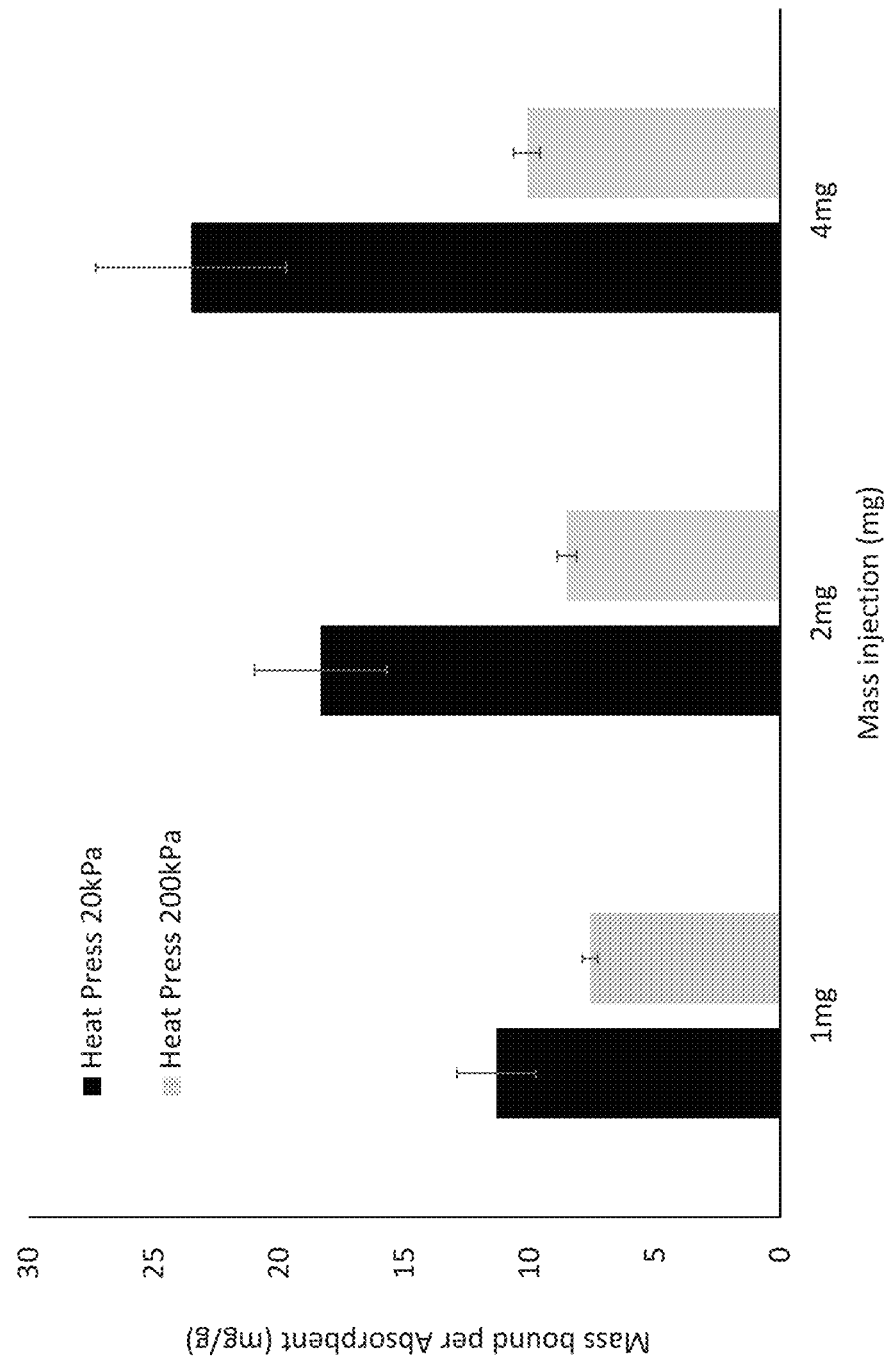
FIG. 9 shows the effect of pressure on the dynamic binding capacity of membranes in accordance with the invention.

"20 kPa" and "200 kPa" regenerated cellulose discs were functionalised with DEAE using the method of Example 3. Dynamic binding capacities (DBC) for these discs were determined using a protocol similar to that set out in Example 5. Dynamic binding capacity (DBC) was determined at a flow of 30 ml/min, using different masses of BSA (1 mg, 2 mg, 4 mg), using Tris-HCl buffer at pH 8, with a IM NaCl elution step. The results of the DBC analysis are shown in FIG. 9. The DBC of the "20 kPa" discs is higher than that of the "200 kPa" discs.

Example 10

Nanofibre discs were prepared according to the method of Preparative Example 2. Discs were deacetylated and immersed with DEACH at room temp, then washed with room temperature 0.5M NaOH. The immersion in DEACH and washing with 0.5M NaOH was repeated up to 5 times and is referred to below as the number of cycles of functionalisation. Thus, discs were functionalised using 1 cycle, 2 cycles, 3 cycles, 4 cycles and 5 cycles.

Figure 10:
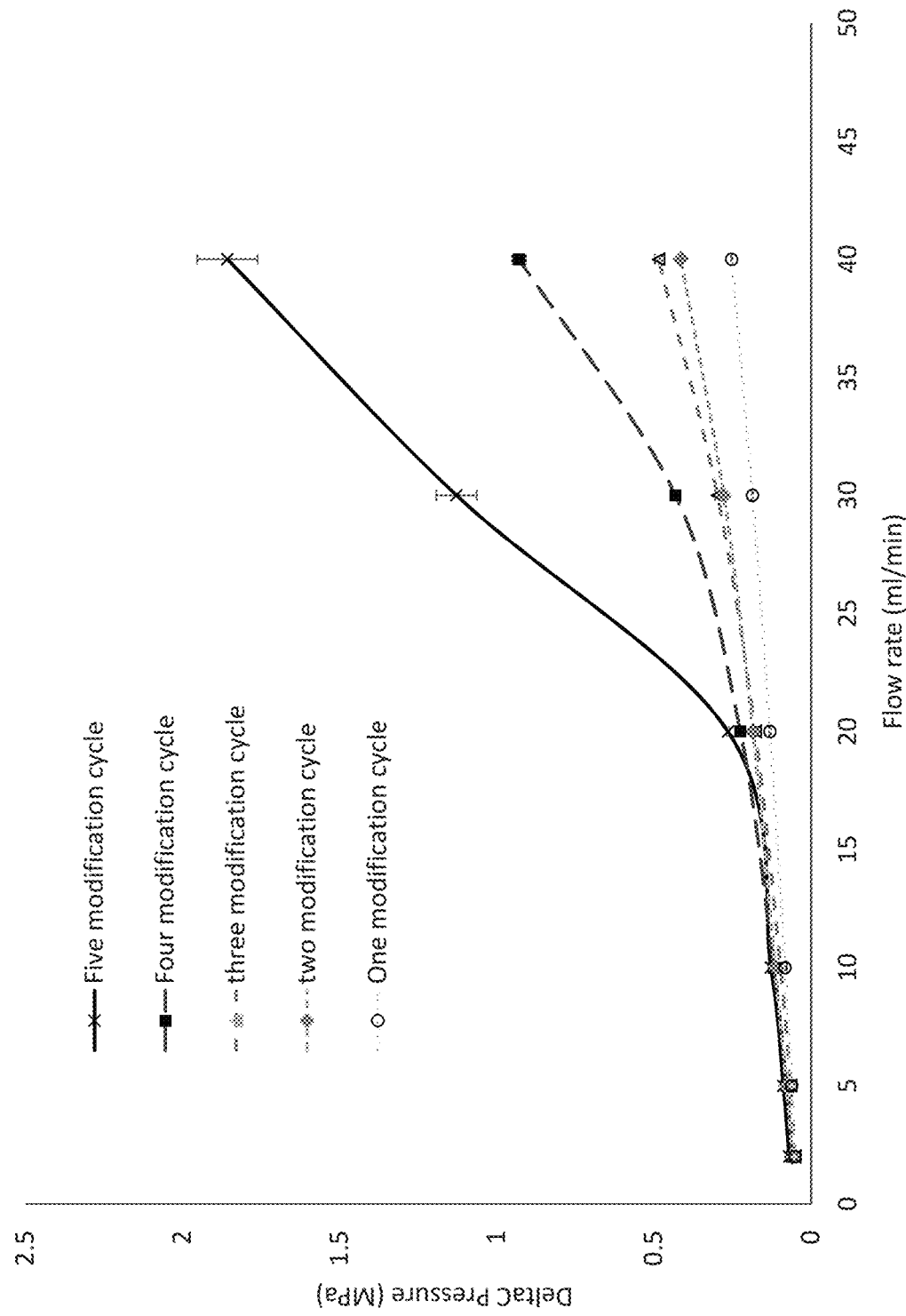
FIG. 10 shows the effect of the number of functionalisation cycles on the flow properties of membranes in accordance with the invention.

The flow characteristics of the 1, 2, 3, 4 and 5 cycle discs were analysed using the method described in Analytical Example 1 using increasing flow rates (2, 5, 10, 20, 30, 40, 60, 80 ml/min), using Tris-HCl buffer at pH 8. The data obtained is shown as FIG. 10. It can be seen that pressure drop increases with the number of cycles.

Figure 11:
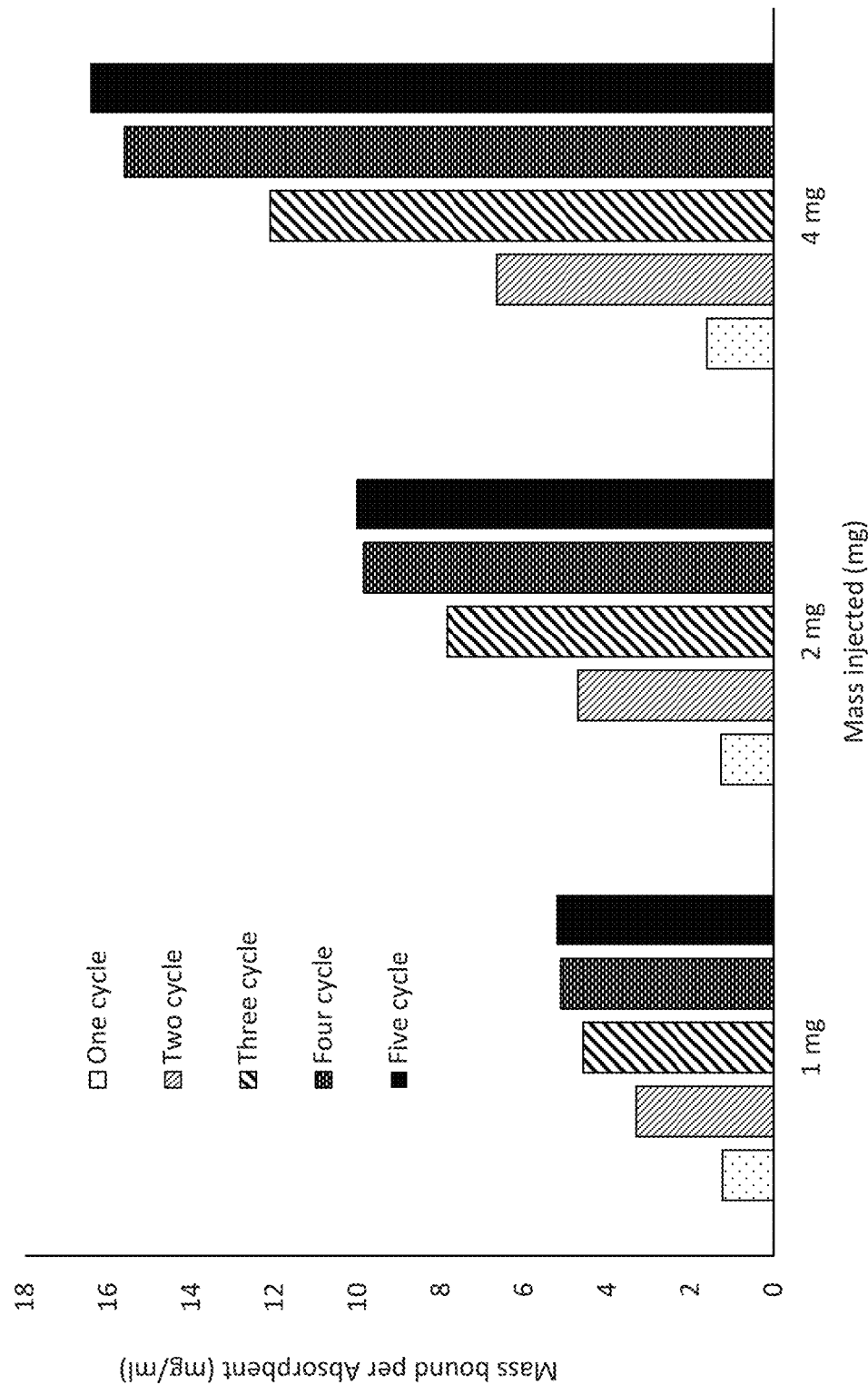
FIG. 11 shows the effect of the number of functionalisation cycles on the dynamic binding capacity of membranes in accordance with the invention.

The dynamic binding capacities (DBC) for the 1, 2, 3, 4 and 5 cycle discs were analysed using the method described in Analytical Example 2. The results of the DBC analysis are shown in FIG. 11. The DBC increases from 1 to 4 cycles, and then decreases for the fifth cycle.

Example 11

Reparation of SP Functionalised Discs

Regenerated cellulose discs were prepared using the method of Preparative Example 2 and Example 1.

To a solution of 10 ml DMSO and 5 mL 1M NaOH was added 2 mL allyl glycidyl ether followed by 10 regenerated cellulose fibre discs. A solution of sodium disulfite (3 g) in 30 mL H2O was adjusted to pH 6.5 by addition of NaOH (1M). The discs obtained in the first step above were then treated with this mixture. The discs were then washed with 0.1M HCl followed by water.

Figure 12:
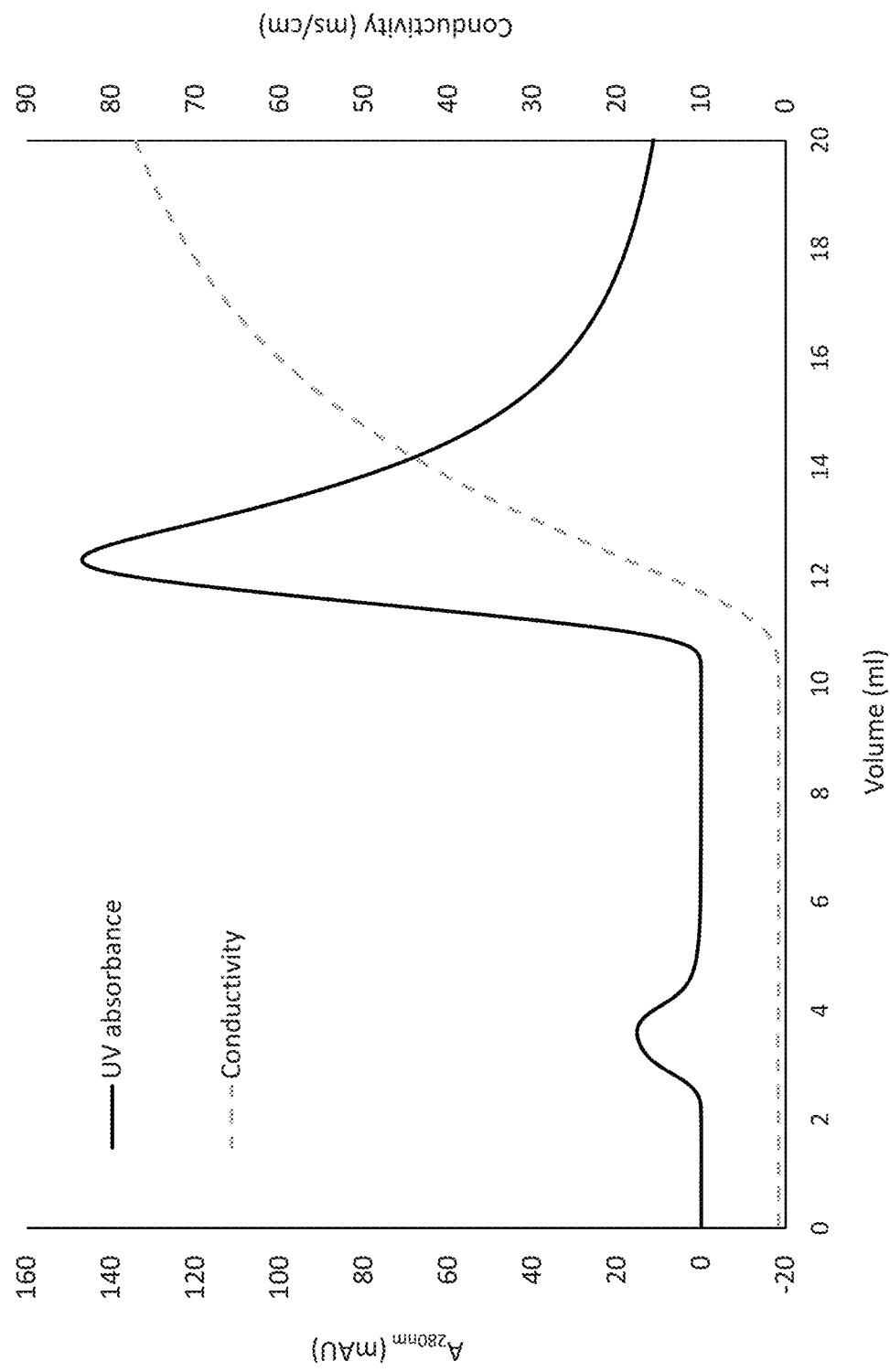
FIG. 12 shows the bind elute properties of a SP-functionalised membrane of the invention.

To determine the dynamic binding capacity, SP-functionalised discs were analysed using a method similar to that outlined above in Example 5. An AKTA purification system (GE Healthcare) was equilibrated with 10 mM Na acetate 5 pH buffer. A sample of 1 mg/ml Lysozyme was loaded onto the system at 30 mL/min. A solution of 1 M NaCl (10 mM Na acetate 5 pH buffer) was used for the elution. The online UV trace at 280 nm produced the chromatogram shown in FIG. 12.

Example 12

Preparation of CM Functionalised Disc

Regenerated cellulose discs were prepared using the method of Preparative Example 2 and Example 1.

These were added to an aqueous solution of NaBr (24.3 mmol) and TEMPO (1.60 mmol) and adjusted using NaOH to pH 10. To this NaOCl was added (5.0 mmol) until there was no further change in pH. Discs were then washed with EtOH.

Figure 13:
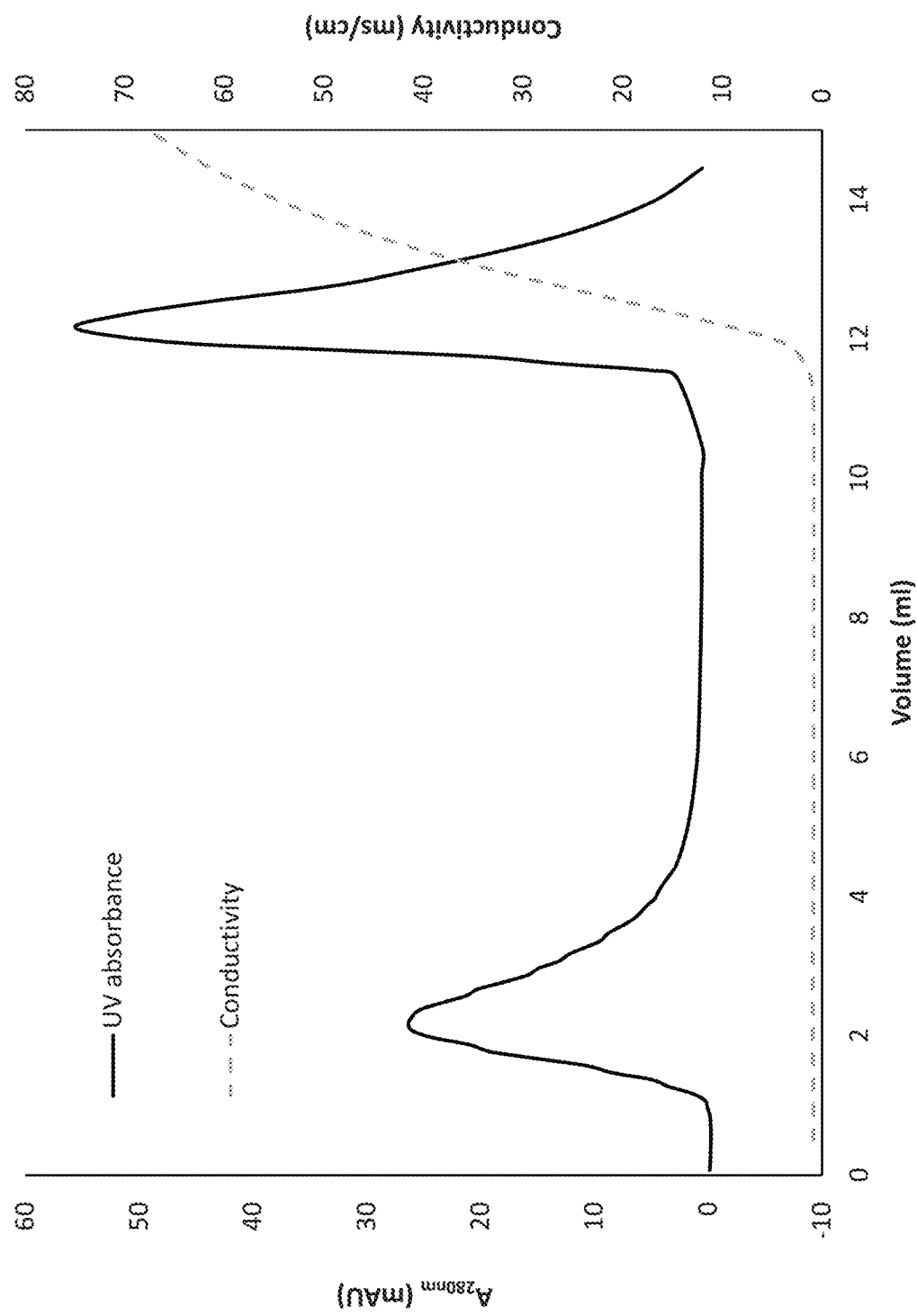
FIG. 13 shows the bind elute properties of a CM-functionalised membrane of the invention.

To determine the dynamic binding capacity of the discs, the AKTA system is run at a flow rate of 30 ml/min and the sample used is Lysozyme at a concentration of 1 mg/ml with load injection of 1 ml. 10 mM Sodium acetate 5 pH buffer was used to equilibrate and wash the system. A solution of 1 M NaCl (10 mM Sodium acetate pH 5 buffer) is used for the elution. The online UV trace at 280 nm produced the chromatogram shown in FIG. 13.

Example 13

Preparation of Q Functionalised Discs

Regenerated cellulose discs were prepared using the method of Preparative Example 2 and Example 1.

These were added to a solution of 2:1:0.1 DMSO:1M NaOH:glycidyltrimethylammonium. The discs were then washed with 0.1M HCl and water.

Figure 14:
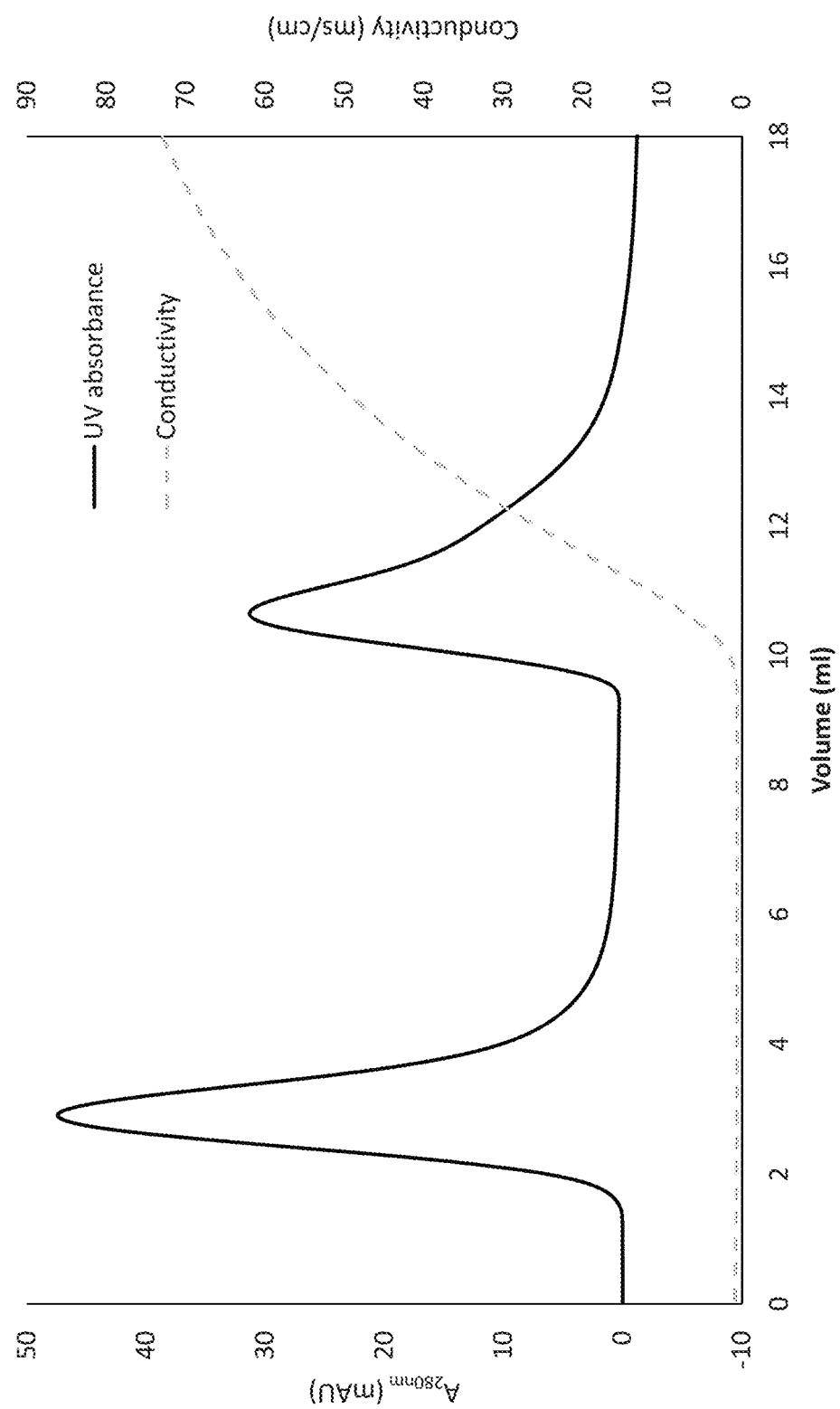
FIG. 14 shows the bind elute properties of a Q-functionalised membrane of the invention.

To determine dynamic binding capacity the AKTA purification system (GE Healthcare) was equilibrated with 10 mM Tris-HCl pH 8 buffer. A sample of 1 mg/ml BSA was loaded onto the system at 20 mL/min. A solution of 1 M NaCl (10 mM Tris-HCl pH 8 buffer) is used for the elution. The online UV trace at 280 nm produced the chromatogram shown in FIG. 14.

Example 14

Protein A Functionalised Discs

Regenerated cellulose discs were prepared using the method of Preparative Example 2 and Example 1.

These were added to an 80 mL solution of sodium acetate buffer (pH 5.5) that contained 6.5 g $NaIO_4$. The discs were then washed with 50 mL ethylene glycol followed by water. Discs were then washed with 0.05% Triton X-100, 100 mM carbonate/bicarbonate pH 9.0. The Protein A ligand was dialyzed with 0.05% Triton X-100, 100 mM carbonate/bicarbonate pH 9.0 and then added to the discs. The solution was then decanted and 0.05% Triton X-100, 100 mM carbonate/bicarbonate pH 9.0 added. To this a 100 mM sodium borohydride solution was added to yield a final borohydride concentration of 4 mM. This solution is then decanted and 20% ethanol in 50 mM phosphate 150 mM sodium chloride pH 6.7 buffer added. The above washing steps were repeated 9 times.

Figure 15:
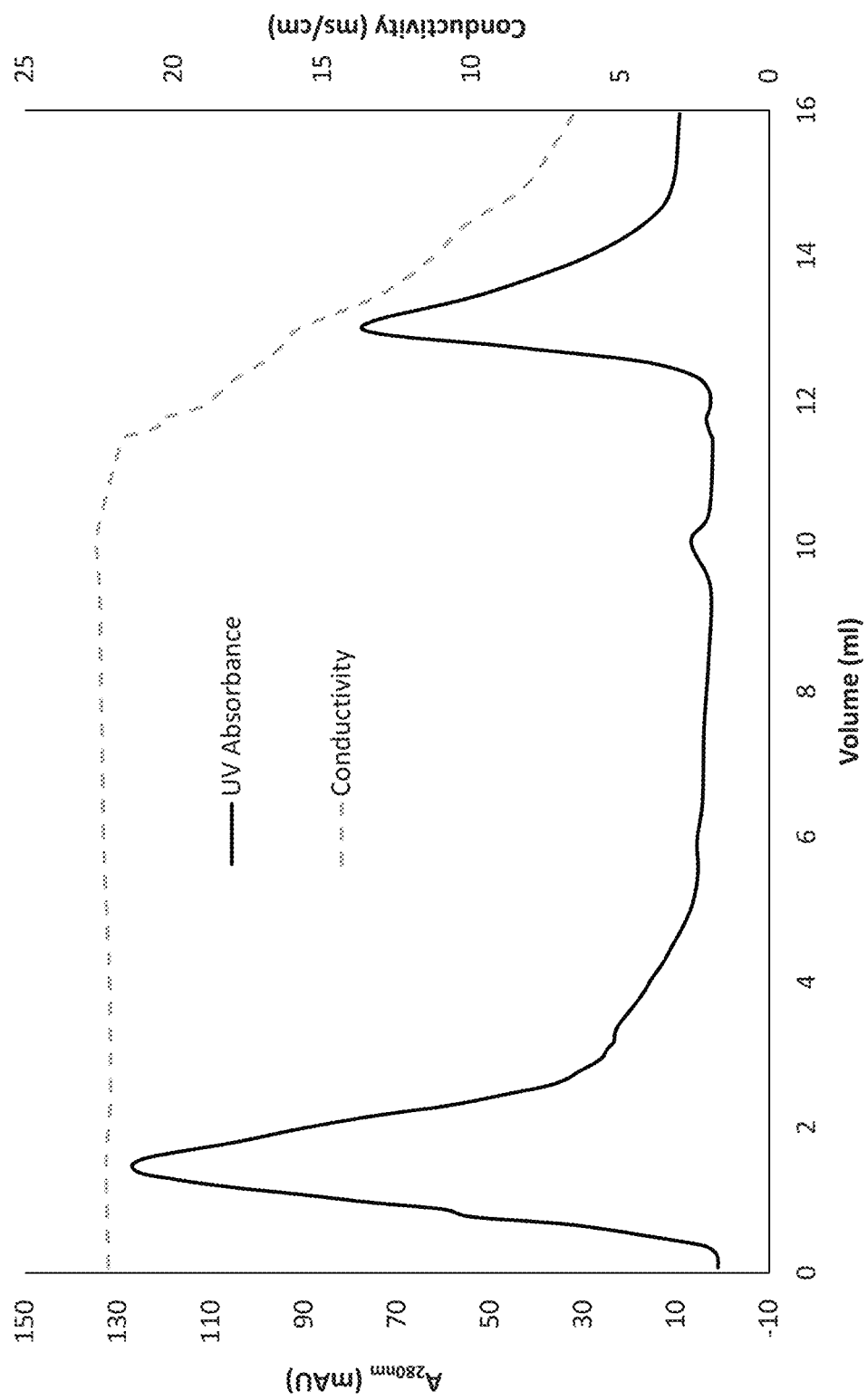
FIG. 15 shows the bind elute properties of a Protein A-functionalised membrane of the invention.

To determine dynamic binding capacity the AKTA system was run at a flow rate of 30 ml/min and the sample used was Protein A purified IgG at a concentration of 1 mg/ml with load injection of 1 ml. PBS pH 7.4 buffer was used to equilibrate and wash the system. A solution of 0.1M Sodium Citrate pH 3.0 buffer is used for the elution. The online UV trace at 280 nm produced the chromatogram shown in FIG. 15.

Example 15

Phenyl Functionalised Discs

Regenerated cellulose discs were prepared using the method of Preparative Example 2 and Example 1.

These were added to 75 mL of a solution of a 2:1 mixture of DMSO:1M NaOH. Styrene oxide (7.5 mL) was then added to the reaction mixture which was stirred at room temperature for 4 hrs. The discs were then washed with methanol, and then water.

To determine dynamic binding capacity the AKTA system was run at a flow rate of 10 ml/min and the sample used was 0.1 mg/ml lysozyme (with 1.5 M ammonium sulphate), with a load injection of 1 ml. 1.5 M ammonium sulphate with 10 mM Tris pH 8 was used to equilibrate and wash the system.

Figure 16:
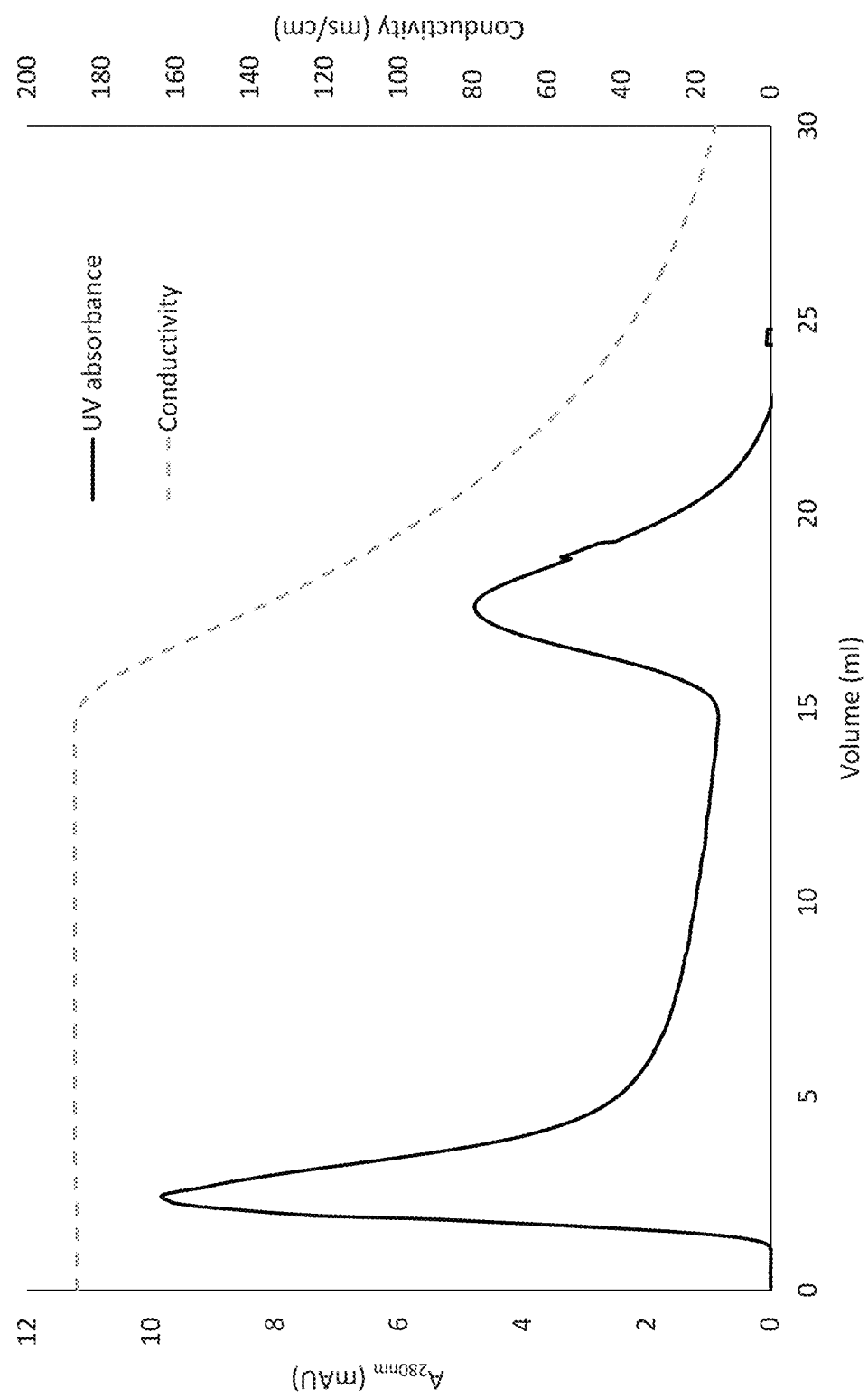
FIG. 16 shows the bind elute properties of a phenyl-functionalised membrane of the invention.

10 mM Tris pH 8 is used for the elution. The online UV trace at 280 nm produced the chromatogram shown in FIG. 16.

Analytical Example 3

Effect of Stacking Before Pressing and Heating

As discussed above in Analytical Example 1, regenerated cellulose discs prepared in accordance with the present invention (the "press" discs) endured for >120 hours in a chemical resistivity test (shown in FIG. 3). The "press" discs showed little degradation even after 120 hours of exposure to NaOH (as shown in FIG. 4).

Single sheets of cellulose acetate nanofibres were obtained as described in Preparative Example 2. A single layer sheet was sandwiched by two plane PTFE sheets and placed in an oven at 208° C. for one hour, according to the method described in Ma, et al, Journal of Membrane Science 265 (2005) 115-123. The obtained sheet was deacetylated using the method outlined in Example 3. Ten discs were cut from the resultant cellulose sheet and stacked together as described in Ma, et al. Samples prepared in this way are referred to below as the "Ma, et al" samples. This process was repeated eight times to create eight ten disc stacks.

A "Ma, et al" ten disc stack was placed in a rubber O-ring and subjected to the chemical resistivity test described above in Analytical Example 1. This was repeated three times. The three "Ma, et al discs" tested failed after ten minutes, ten minutes and two minutes, respectively.

It can be seen from these results that discs that are formed from multiple non-woven sheets of nanofibres which are first stacked and then pressed and heated simultaneously have superior chemical resistivity to those formed by heating individual nanofibre sheets, followed by subsequent stacking.

Figure 17:
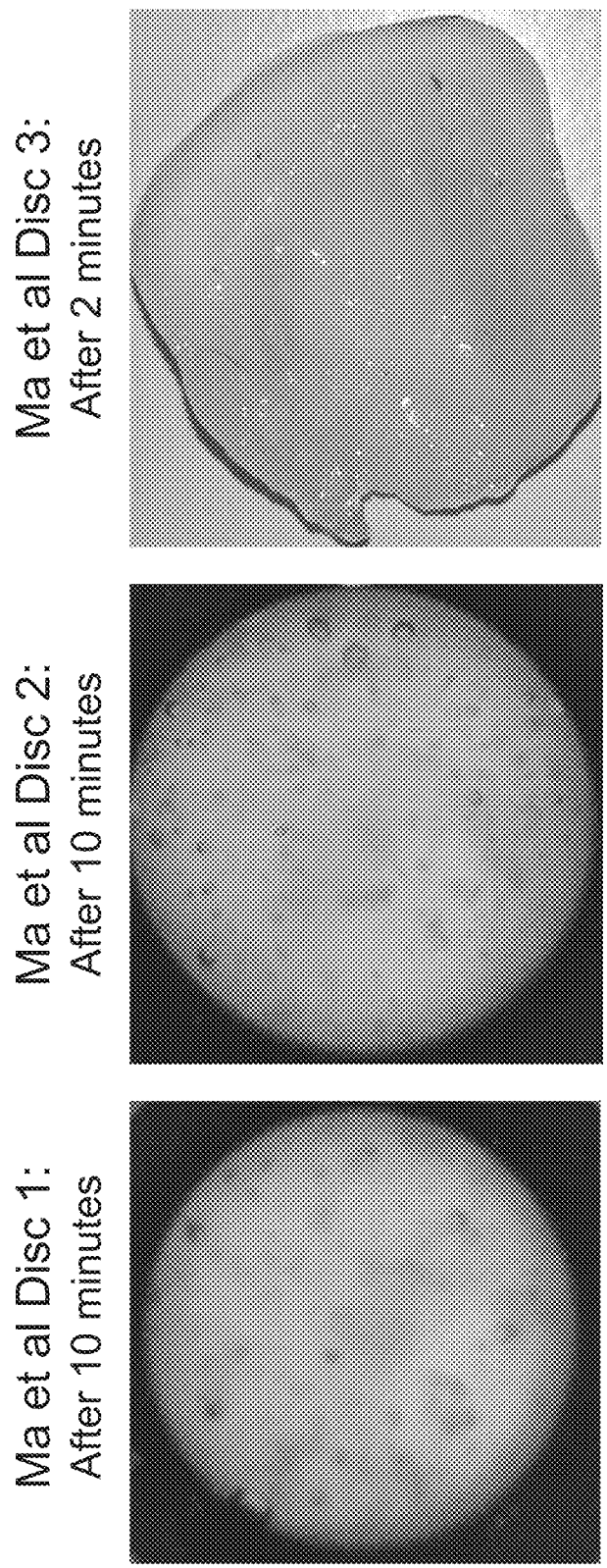
FIG. 17 shows photographs of membranes not in accordance with the invention following exposure to NaOH.

The "Ma, et al" discs showed discolouration and pitting within 10 minutes of exposure to IM NaOH as shown in FIG. 17. The "heat press" disc showed little degradation even after 120 hours of exposure (FIG. 4).

Figure 18:
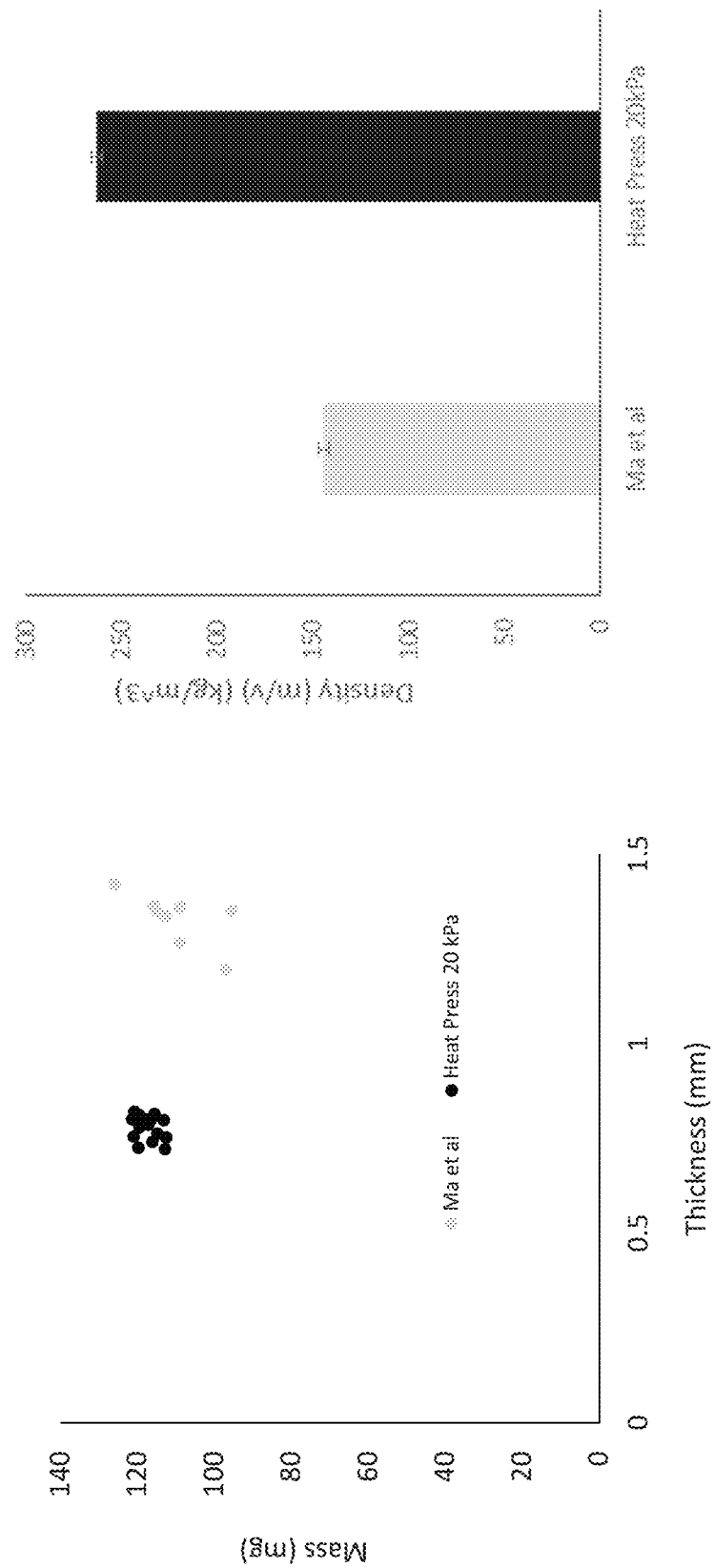
FIG. 18 shows the thickness and densities of membranes not in accordance with the invention and membranes in accordance with the invention.

The thickness and density of a number of "heat press" and "Ma, et al" discs were determined. The thicknesses and average densities of these discs are shown in FIG. 18. The "heat press" discs were found to be both thinner and denser than the "Ma, et al" discs.

Figure 19:
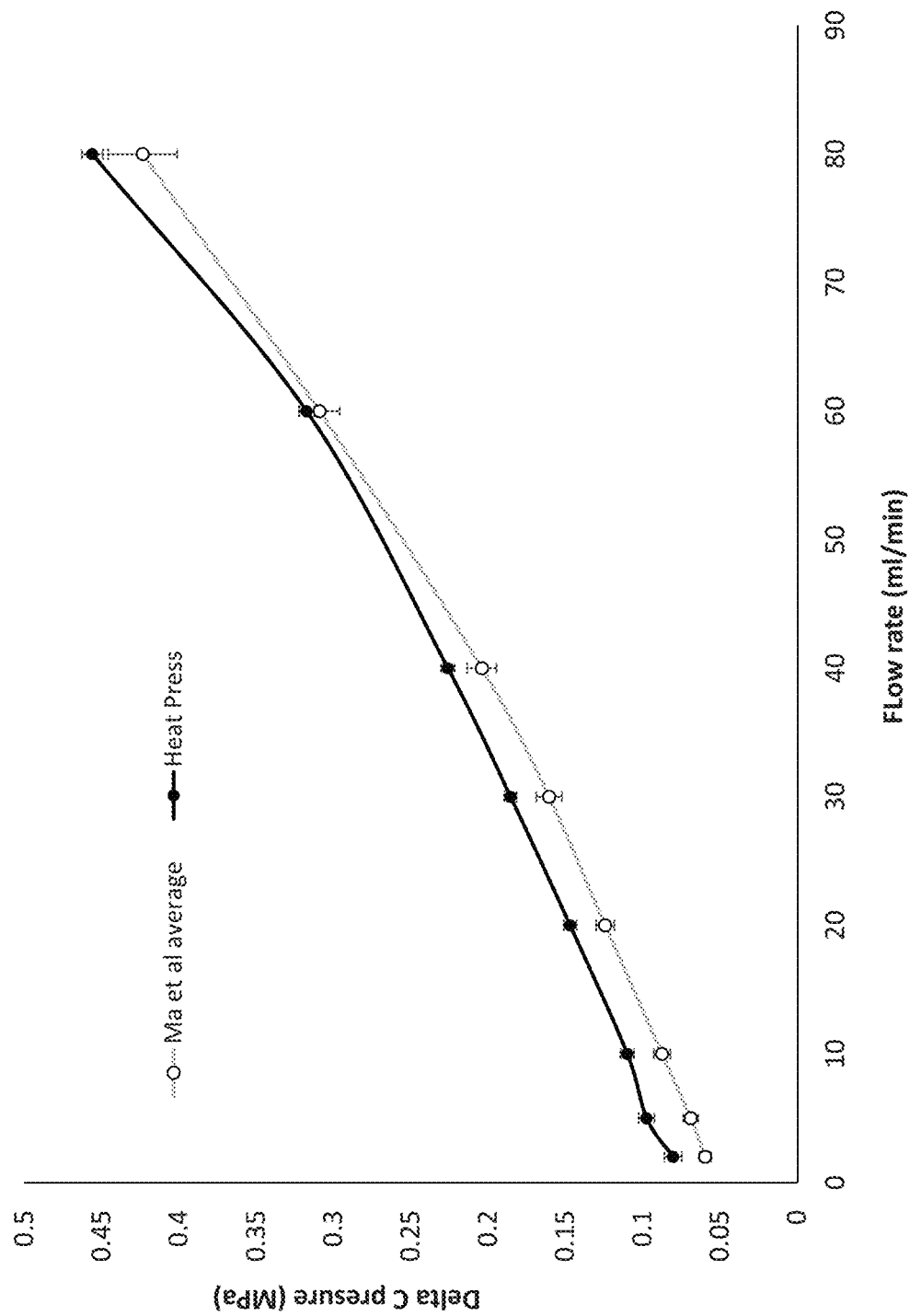
FIG. 19 shows the flow properties of membranes not in accordance with the invention and membranes in accordance with the invention.

The flow characteristics of "heat press" and "Ma, et al" discs were analysed by determining the delta column pressure drop at increasing flow rates of Tris-HCl buffer (pH 8) through the discs. The data obtained is shown as FIG. 19. It can be seen that the "heat press" and "Ma, et al" discs have similar flow characteristics.

Figure 20:
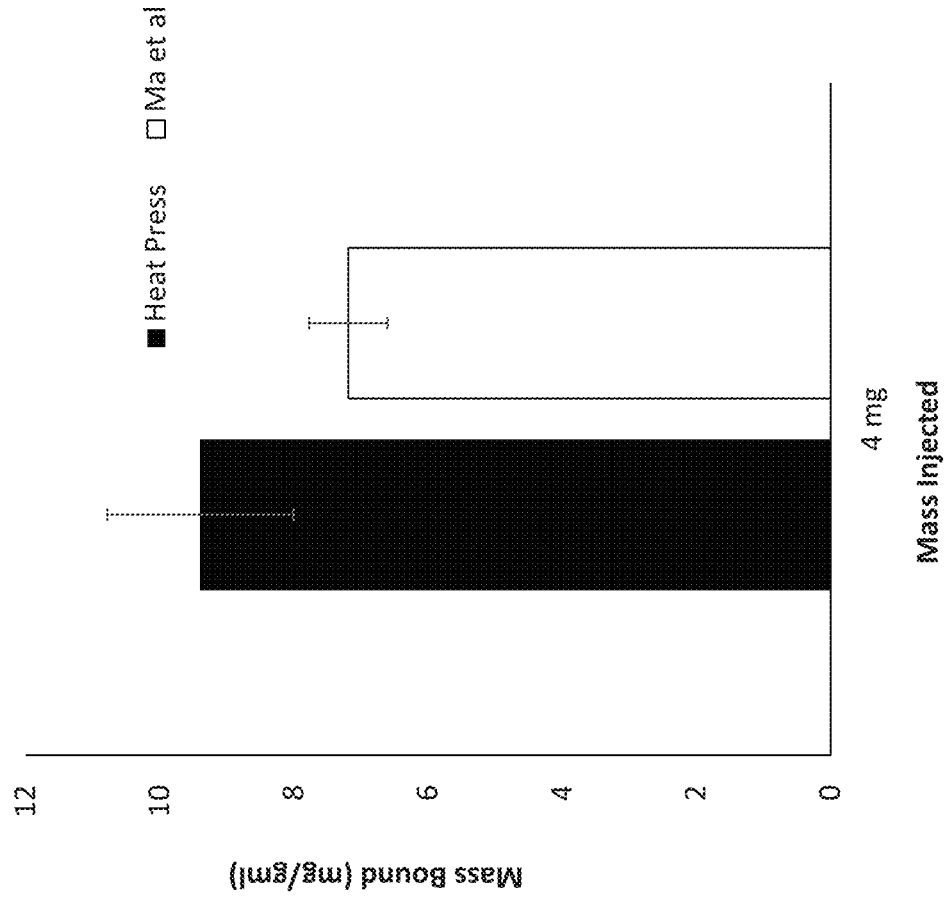
FIG. 20 shows the dynamic binding capacity of membranes not in accordance with the invention and membranes in accordance with the invention.

"Heat press" and "Ma et al" discs were functionalised with DEAE ligands using the method described in Example 3. The dynamic binding capacity of these discs was determined using a protocol similar to that set out in Example 5. Dynamic binding capacity (DBC) was determined at a flow of 30 ml/min, using different masses of BSA (1 mg, 2 mg, 4 mg), using Tris-HCl buffer at pH 8, with a 1M NaCl elution step. The results of the DBC analysis are shown in FIG. 20. The DBC of the "heat press" discs is higher than that of the "Ma, et al" discs.

Figure 21:
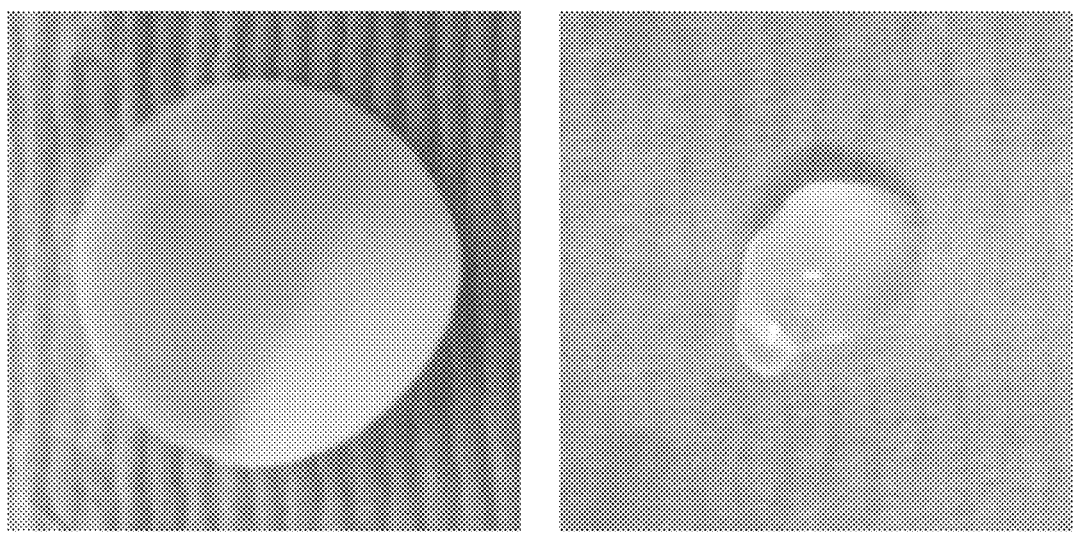
FIG. 21 shows photographs of a membrane in accordance with the invention (top image) and a membrane not in accordance with the invention (bottom image) following multiple functionalisation cycles.

The possibility of performing repeat functionalisations of the "heat press" and "Ma, et al" discs was determined. The method for repeat DEAE functionalisation of the discs described in Example 10 was carried out on both the "heat press" and "Ma, et al" regenerated cellulose discs. The poor chemical stability of the "Ma, et al" material meant it was not possible to increase the DBC by using multiple functionalisation cycles. The maximum DBC that was found to be possible for the "Ma, et al" material was around 7 mg/ml (as shown in FIG. 20). By using multiple functionalisation cycles it was possible to increase the DBC of the "heat press" material to around 16 mg/ml (see FIG. 11). The "Ma, et al" material degraded significantly after multiple DEAE cycles. This problem was not observed with the "heat press" material. Photographs of the "Ma, et al" and "heat press" material after multiple functionalisation cycles are shown in FIG. 21. The "Ma, et al" material is shown as the bottom photograph, and the "heat press" material as the top photograph in FIG. 21.

Some preferred embodiments of the present invention are set out below.

[1] A process for preparing a functionalised cellulose chromatography medium, which process comprises (i) providing one or more non-woven sheets, each comprising one or more cellulose acetate nanofibres, (ii) pressing the one or more non-woven sheets, (iii) heating the one or more non-woven sheets to fuse points of contact between sections of the one or more cellulose acetate nanofibres, (iv) treating the pressed and heated product to convert the cellulose acetate to cellulose, and (v) contacting the thus-obtained product in a batchwise fashion between two and four times with a reagent which functionalises the product of step (iv) as a chromatography medium.

[2] The process according to [1], each step of contacting with a reagent comprising (a) contacting with the reagent, (b) isolating the product of step (a) from the reagent, (c) optionally treating the product of step (b) with aqueous alkali, and (d) optionally washing the product of step (b)/(c) with water.

[3] The process according to [1] or [2], step (v) comprising (1) (a1) contacting the product of step (iv) with the reagent, (b1) isolating the product of step (a1) from the reagent, (c1) optionally treating the product of step (b1) with aqueous alkali, and (d1) optionally washing the product of step (b1)/(c1) with water, and (2) (a2) contacting the product of step (b1)/(c1)/(d1) with the reagent, (b2) isolating the product of step (a2) from the reagent, (c2) optionally treating the product of step (b2) with aqueous alkali, and (d2) optionally washing the product of step (b2)/(c2) with water; or (1) (a1) contacting the product of step (iv) with the reagent, (b1) isolating the product of step (a1) from the reagent, (c1) optionally treating the product of step (b1) with aqueous alkali, and (d1) optionally washing the product of step (b1)/(c1) with water, (2) (a2) contacting the product of step (b1)(c1)/(d1) with the reagent, (b2) isolating the product of step (a2) from the reagent, (c2) optionally treating the product of step (b2) with aqueous alkali, and (d2) optionally washing the product of step (b2)/(c2) with water, and (3) (a3) contacting the product of step (b2)/(c2)/(d2) with the reagent, (b3) isolating the product of step (a3) from the reagent, (c3) optionally treating the product of step (b3) with aqueous alkali, and (d3) optionally washing the product of step (b3)/(c3) with water, or (1) (a1) contacting the product of step (iv) with the reagent, (b1) isolating the product of step (a1) from the reagent, (c1) optionally treating the product of step (b1) with aqueous alkali, and (d1) optionally washing the product of step (b1)/(c1) with water, (2) (a2) contacting the product of step (b1)/(c1)/(d1) with the reagent, (b2) isolating the product of step (a2) from the reagent, (c2) optionally treating the product of step (b2) with aqueous alkali, and (d2) optionally washing the product of step (b2)/(c2) with water, (3) (a3) contacting the product of step (b2)/(c2)/(d2) with the reagent, (b3) isolating the product of step (a3) from the reagent, (c3) optionally treating the product of step (b3) with aqueous alkali, and (d3) optionally washing the product of step (b3)/(c3) with water, and (4) (a4) contacting the product of step (b3)/(c3)/(d3) with the reagent, (b4) isolating the product of step (a4) from the reagent, (c4) optionally treating the product of step (b4) with aqueous alkali, and (d4) optionally washing the product of step (b4)/(c4) with water.

[4] The process according to any one of the preceding embodiments, each step of contacting with a reagent being for a period of time from 1 to 20 minutes.

[5] A process for preparing a functionalised cellulose chromatography medium, which process comprises (i) providing one or more non-woven sheets, each comprising one or more cellulose acetate nanofibres, (ii) pressing the one or more non-woven sheets, (iii) heating the one or more non-woven sheets to fuse points of contact between sections of the one or more cellulose acetate nanofibres, (iv) treating the pressed and heated product to convert the cellulose acetate to cellulose, (v) placing the thus-obtained product in a holder, and (vi) causing a reagent to flow through the holder so that the reagent flows in contact with the product obtained in step (iv) which functionalises the product of step (iv) as a chromatography medium.

[6] The process according to [5], step (vi) comprising
causing a reagent to flow through the holder under pressure; and/or
causing a reagent to flow through the holder using a pump; and/or
causing a reagent to flow through the holder in a cyclical manner; and/or
causing a reagent to flow through the holder for a period of time from 1 to 20 minutes.

[7]. The process according to [6] or [7] additionally comprising the step of treating the product of step (vi) with aqueous alkali, and optionally washing the thus-obtained product with water.

[8] The process according to any one of the preceding embodiments, the functionalised cellulose chromatography medium being suitable for use in a chromatography method chosen from ion exchange, affinity capture or hydrophobic interaction methods.

[9] The process according to [8],
the chromatography method being a cationic exchange method, and the chromatography medium being functionalised with one or more carboxylate, sulphonate or phosphonate groups;
the chromatography method being an anionic exchange method, and the chromatography medium being functionalised with one or more quaternary amino or diethylamine groups, preferably one or more DEAE groups;
the chromatography method being an affinity capture chromatography method, and the chromatography medium being functionalised with one or more proteins, peptides, antibodies or fragments thereof, dyes, histidine, or groups containing a metal cation; or
the chromatography method being a hydrophobic interaction chromatography method, and the chromatography medium being functionalised with one or more propyl, butyl, phenyl, or octyl groups.

[10] The process according to any one of the preceding embodiments, wherein one or more hydroxyl groups on the cellulose chromatography medium are functionalised.

[11] The process according to any one of the preceding embodiments, the one or more cellulose nanofibres having a mean diameter of 10 nm to 1000 nm.

[12] The process according to any one of the preceding embodiments, the step of pressing the one or more non-woven sheets employing a pressure of 0.01 to 5 MPa.

[13] The process according to any one of the preceding embodiments, the step of heating the one or more non-woven sheets employing a temperature of from 200 to 220° C.

[14] A process for preparing a functionalised polymeric chromatography medium, which process comprises (I) providing one or more polymer nanofibres, (II) pressing the one or more polymer nanofibres, (III) heating the one or more polymer nanofibres to fuse points of contact between sections of the one or more polymer nanofibres, and (IV) contacting the pressed and heated product with a reagent which functionalises the product of step (III) as a chromatography medium.

[15] A process for preparing a functionalised polymeric chromatography medium, which process comprises (I) providing one or more polymer nanofibres, (II) optionally pressing the one or more polymer nanofibres, (III) optionally heating the one or more polymer nanofibres to fuse points of contact between sections of the one or more polymer nanofibres, and (IV) contacting the product of step (I), (II) or (III) in a batchwise fashion at least two times with a reagent which functionalises the product of step (I), (II) or (III) as a chromatography medium.

[16] A process for preparing a functionalised polymeric chromatography medium, which process comprises (I) providing one or more polymer nanofibres, (II) optionally pressing the one or more polymer nanofibres, (III) optionally heating the one or more polymer nanofibres to fuse points of contact between sections of the one or more polymer nanofibres, (IV) placing the product of step (I), (II) or (III) in a holder, and (V) causing a reagent to flow through the holder so that the reagent flows in contact with the product of step (I), (II) or (III) which functionalises the product of step (I), (II) or (III) as a chromatography medium.

[17] The process according to any one of [14] to [16], the functionalised chromatography medium being suitable for use in a chromatography method defined in claim [8] or [9].

[18] The process according to any one of [14] to [16], wherein one or more hydroxyl, amino or carboxylic acid groups on the chromatography medium are functionalised.

[19] The process according to any one of [14] to [16], the polymer being chosen from cellulose, cellulose acetate, polysulfones, polyamides, polyacrylic acid, polymethacrylic acid, polyacrylonitrile, polystyrene, polyethylene oxide, and mixtures thereof.

[20] A functionalised chromatography medium obtainable by the process according to any one of the preceding embodiments.

[21] A process for preparing a chromatography cartridge, which process comprises carrying out the process of any one of [1] to [19] and incorporating the thus-obtained product into a cartridge.

[22] A chromatography cartridge which (a) is obtainable by the process of [21], or (b) which comprises one or more functionalised chromatography media according to [20].

[23] Use of a functionalised chromatography medium according to [20] or a chromatography cartridge according to [22] in chromatography.

[24] A process for isolating one or more biological molecules from a mobile phase, which process comprises contacting one or more biological molecules in a mobile phase with a functionalised chromatography medium according to [20] or a chromatography cartridge according to [22].

[25] The process according to [24], which is an ion exchange, affinity capture or hydrophobic interaction chromatography process.

The invention claimed is:

1. A process for preparing a functionalised polymeric chromatography medium, which process comprises
   (I) providing a stack of two or more non-woven sheets stacked one on top of the other, each said sheet consisting essentially of one or more polymer nanofibres,
   (II) simultaneously heating and pressing the stack of sheets to fuse points of contact between the nanofibres of adjacent sheets to form a pressed and heated product, and
   (III) contacting the pressed and heated product of step (II) in a batchwise fashion in a plurality of batches with a respective batch reagent associated with each batch of the plurality of batches, said respective batch reagent being same or different in the plurality of batches, to cause the respective batch reagent to be partially retained within the polymer nanofibers and generate the functionalized polymeric chromatography medium,
   wherein a pressure of between 1 kPa to 500 kPa is applied to the stack of sheets in step (II) and wherein the stack of sheets is heated at a temperature between 190° and 220° in step (II), and
   wherein the pressed and heated product is treated to deprotect or activate any functional groups on the one or more polymer nanofibers prior to the step of contacting with the respective batch reagent.

2. The process according to claim 1, wherein between two and thirty said sheets are stacked one on top of the other in step (I); or wherein between five and twenty five said sheets are stacked one on top of the other in step (I).

3. The process according to claim 1, wherein each non woven sheet consists of a single polymer nanofibre, or comprises 2, 3, 4, 5, 6, 7, 8, 9 or 10 polymer nanofibres.

4. The process according to claim 1, wherein the polymer is selected from the group consisting of cellulose, cellulose acetate, polysulfones, polyamides, polyacrylic acid, polymethacrylic acid, polyacrylonitrile, polystyrene, polyethylene oxide, and mixtures thereof.

5. The process according to claim 1, wherein the said nanofibres are cellulose acetate nanofibres, and the pressed and heated product is treated between steps (II) and (III) to convert the cellulose acetate to cellulose.

6. The process according to claim 1, wherein the stack of sheets is heated at a temperature between 200° and 220° C. in step (II).

7. The process according to claim 1, each step of contacting with the respective batch reagent in a respective batch of the plurality of batches comprising (a) contacting with the respective batch reagent, (b) isolating the product of step (a) from the reagent, (c) treating the product of step (b) with aqueous alkali, and (d) washing the product of step (c) with water.

8. The process according to claim 1, wherein the plurality of batches comprises between two and four batches.

9. The process according to claim 1, step (III) comprising placing the pressed and heated product of step (II) in a holder, and (IV) causing the respective batch reagent to flow through the holder so that the respective batch reagent flows in contact with the pressed and heated product of step (II) which functionalises the product of step (II) as a chromatography medium.

10. The process according to claim 9, wherein step (IV) comprises
    causing the respective batch reagent to flow through the holder under pressure; and/or
    causing the respective batch reagent to flow through the holder using a pump; and/or
    causing the respective batch reagent to flow through the holder in a cyclical manner; and/or
    causing the respective batch reagent to flow through the holder for a period of time from 1 to 20 minutes.

11. The process according to claim 1, wherein the respective batch reagent functionalises the pressed and heated product so that the resultant functionalised chromatography medium is suitable for use in a chromatography method chosen from the group consisting of ion exchange, affinity capture, hydrophobic interaction and mixed mode methods.

12. The process according to claim 1, wherein one or more polymer nanofibers comprise hydroxyl, amino, or carboxy groups, and wherein the respective batch reagent functionalises the hydroxyl, amino or carboxylic acid groups.

13. The process according to claim 1, wherein
    between five and twenty five said sheets are stacked one on top of the other in step (I), each sheet comprising 1, 2 or 3 polymer nanofibres, and each sheet having a thickness of from 5 to 40 μm, and/or
    in step (II) a temperature below the melting point of the polymer at between 190° and 220° and a pressure of from 1 kPa to 500 kPa are applied for 1 to 120 minutes so as to obtain a pressed and heated product having an average density of 250 to 750 kg/m$^3$ and a thickness of 0.05 to 10 mm.

14. The process according to claim 1, wherein
    between five and twenty said sheets are stacked one on top of the other in step (I), each sheet consisting of a single polymer nanofibre, and each sheet having a thickness of from 5 to 120 μm and an area density of from 1 to 40 g/m$^2$, and/or
    in step (II) a temperature below the melting point of the polymer and a pressure of from 1 to 500 kPa are applied for 1 to 30 minutes so as to obtain a pressed and heated product having an average density of 200 to 1000 kg/m$^3$ and a thickness of 0.05 to 10 mm.

* * * * *